United States Patent
Yeh et al.

(12) 
(10) Patent No.: US 6,312,946 B1
(45) Date of Patent: *Nov. 6, 2001

(54) VIABLE CONTAMINANT PARTICLE FREE ADENOVIRUSES, THEIR PREPARTION AND USE

(75) Inventors: Patrice Yeh, Paris; Michel Perricaudet, Ecrosnes; Cécile Orsini, Paris, all of (FR)

(73) Assignee: Rhone-Poulenc Rorer S.A., Antony (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,575

(22) PCT Filed: Oct. 25, 1995

(86) PCT No.: PCT/FR95/01415

§ 371 Date: Apr. 22, 1997

§ 102(e) Date: Apr. 22, 1997

(87) PCT Pub. No.: WO96/13596

PCT Pub. Date: May 9, 1996

(30) Foreign Application Priority Data

Oct. 28, 1994 (FR) .................................................. 94 13355

(51) Int. Cl.[7] .......................... C12N 15/861; A61K 48/00
(52) U.S. Cl. ...................... 435/320.1; 435/455; 435/456; 424/93.2; 424/93.21; 514/44
(58) Field of Search .............................. 424/93.2, 93.21; 514/44; 435/172.3, 172.1, 91.1, 320.1, 455, 456

(56) References Cited

U.S. PATENT DOCUMENTS 5,670,488 * 9/1997 Gregory et al. ......................... 514/44
5,707,618 * 1/1998 Armentano et al. .............. 424/93.21

FOREIGN PATENT DOCUMENTS

WO 94/24297 10/1994 (WO).
WO 94/26914 11/1994 (WO).
WO 94/28152 12/1994 (WO).

OTHER PUBLICATIONS

Hay et al., "Replication of adenovirus mini–chromosomes", J. Mol. Biol. 175: 493–510, 1984.*

Gräble et al., "Adenovirus type 5 packaging domain is composed of a repleated element that is functionally redundant", J. Virol. 64(5): 2047–2056, May 1990.*

Berkner, "Expression of heterologous sequences in adenoviral vectors", Curr. Topics. Microbiol. Immunol. 158:39–66, 1992.*

Wang et al., Correction of a Deletion Mutant by Gene Targeting with an Adenovirus Vector, Molecular & Cellular Biol., 13(2) 918–927 (1993).

Bett et al., Packaging Capacity and Stability of Human Adenovirus Type 5 Vectors, Journal of Virology, 67(10) 5911–5921 (1993).

* cited by examiner

*Primary Examiner*—Scott D. Priebe
(74) *Attorney, Agent, or Firm*—Finnegan, Henderson, Farabow, Garrett & Dunner, L.L.P.

(57) ABSTRACT

Novel adenovirus-derived viral vectors, the preparation thereof, and their use in gene therapy, are disclosed. In particular, recombinant adenoviruses including an adenovirus genome wherein (i) the E1 region is inactivated, (ii) the genomic organization is modified, and (iii) optional recombination with the producing line genome generates nonviable viral particles, are disclosed.

23 Claims, 23 Drawing Sheets

SINGLE RECOMBINATION AND CHROMOSOME BREAKAGE

DOUBLE RECOMBINATION

SINGLE RECOMBINATION AND CHROMOSOME BREAKAGE

DOUBLE RECOMBINATION pPY88 pGY50' pPY90'

HincP/Ad5[ITRΨdelE1(SacB+SpecR)delE4(Ψ+ITR)]

HincP/Ad5[ITRΔΨdelE1(ORF6+ORF7)delE4(Ψ+ITR)]

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide"

(xi) SEQUENCE DESCRIPTION: SEQ ID NO: 1:

AGATCCTCTA GCTAGAGTCG AC                                              22

(2) INFORMATION FOR SEQ ID NO: 2:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 2:

CGGCGGGAAT TCTTAATTAA CATCATCAAT AATATACCTT ATTTTGG                   47

(2) INFORMATION FOR SEQ ID NO: 3:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 3:

CACCACCTGC AGGGCAGCCA TAACAGTCAG CCTTACC                              37

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 4:

GATATCTGAA GATACAGATT GAG                                             23

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 5:

CGGCCGTTAA ACCGCATTGG GAG                                             23

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid -continued (A) DESCRIPTION: /desc = "Oligonucleotide"

(xi) SEQUENCE DESCRIPTION: SEQ ID NO: 6:

AAGCTTATTG CCATCATTAT GGAC                                                      24

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 7:

ACTAGTTATT TAGGGGTTTT GCGC                                                      24

VIABLE CONTAMINANT PARTICLE FREE ADENOVIRUSES, THEIR PREPARTION AND USE

Figure 1:
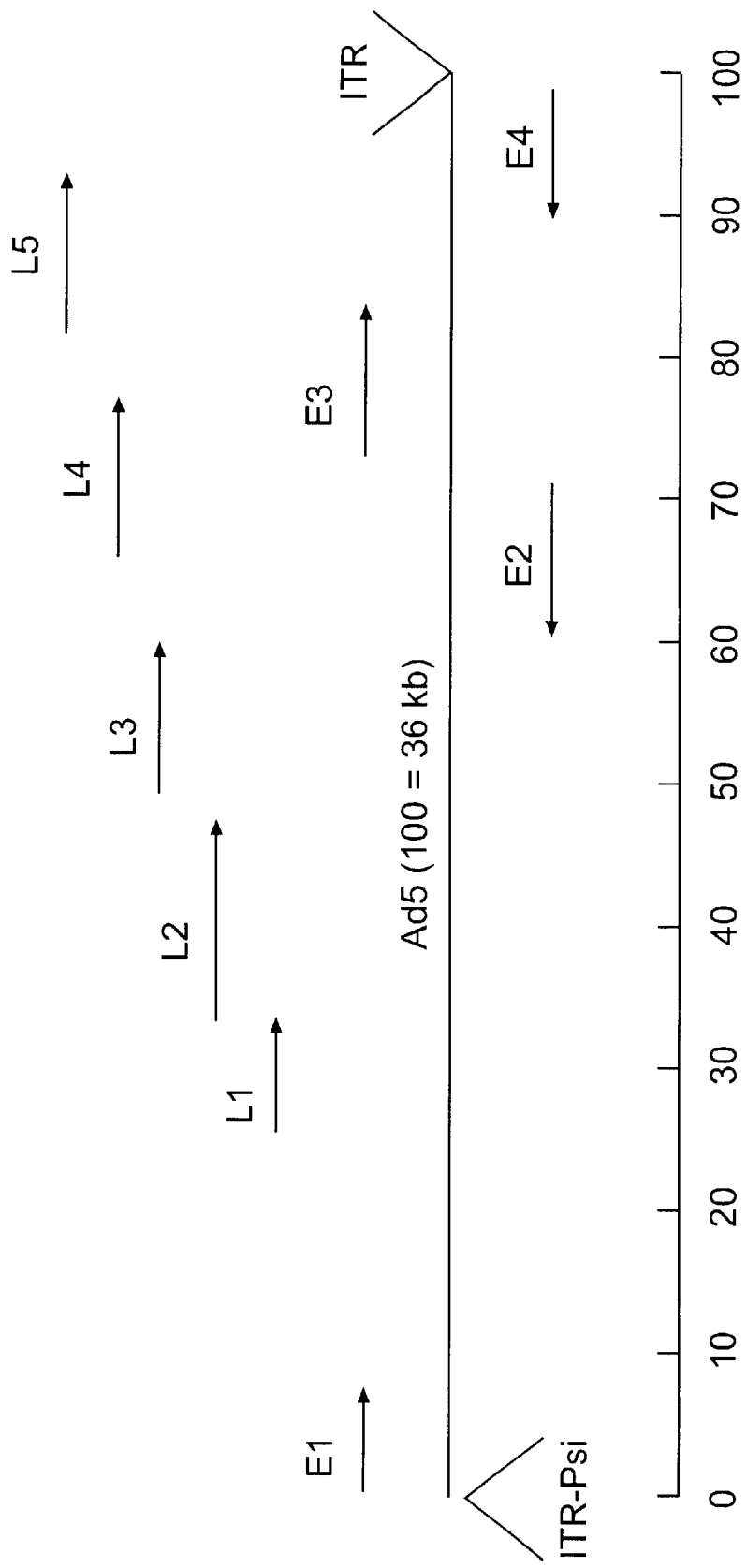

This application is a 371 of International Application PCT/FR95/01415, filed Oct. 25, 1995, and which designated the United States.

The present invention relates to new viral vectors, to their preparation and to their use in gene therapy. It also relates to pharmaceutical compositions containing said viral vectors. More especially, the present invention relates to recombinant adenoviruses as vectors for gene therapy.

Gene therapy consists in correcting a deficiency or an abnormality (mutation, aberrant expression, and the like) by introducing genetic information into the cell or organ affected. This genetic information may be introduced either in vitro into a cell extracted from the organ, the modified cell then being reintroduced into the body, or directly in vivo into the appropriate tissue. In this second case, different techniques exist, including various techniques of transfection involving complexes of DNA and DEAE-dextran (Pagano et al., J. Virol. 1 (1967) 891), of DNA and nuclear proteins (Kaneda et al., Science 243 (1989) 375) and of DNA and lipids (Felgner et al., PNAS 84 (1987) 7413), the use of liposomes (Fraley et al., J. Biol. Chem. 255 (1980) 10431), and the like. More recently, the use of viruses as vectors for gene transfer has been seen to be a promising alternative to these physical transfection techniques. In this connection, different viruses have been tested for their capacity to infect certain cell populations. This applies especially to retroviruses (RSV, EMS, MMS, and the like), the HSV virus, adeno-associated viruses and adenoviruses.

Among these viruses, the adenoviruses display certain properties which are advantageous for use in gene therapy. In particular, they have a fairly broad host range, are capable of infecting resting cells, do not integrate in the genome of the infected cell and have not been associated to date with pathologies of importance in man. Adenoviruses have thus been used to transfer genes of interest to muscle (Ragot et al., Nature 361 (1993) 647), the liver (Jaffe et al., Nature genetics 1 (1992) 372), the nervous system (Akli et al., Nature genetics 3 (1993) 224), and the like.

Adenoviruses are linear double-stranded DNA viruses approximately 36 kb in size. Their genome comprises, in particular, an inverted repeat sequence (ITR) at each end, an encapsidation sequence (Psi), early genes and late genes (see FIG. 1). The main early genes are contained in the E1, E2, E3 and E4 regions. Among these, the genes contained in the E1 region (E1a and E1b in particular) are necessary for viral replication. The E4 and L5 regions, for example, are for their part, involved in viral propagation. The main late genes are contained in the L1 to L5 regions. The genome of the Ad5 adenovirus has been sequenced completely, and is accessible on a database (see, in particular, Genebank M73260). Likewise, some portions, or even the whole, of the genome of adenoviruses of different serotypes (Ad2, Ad7, Ad12, and the like) have also been sequenced.

In view of the properties of the adenoviruses mentioned above, the latter have already been used for the transfer of genes in vivo. To this end, different vectors derived from adenoviruses have been prepared, incorporating different genes (β-gal, OTC, $\alpha_1$-AT, cytokines, and the like). In each of these constructions, the adenovirus has been modified so as to make it incapable of replication in the infected cell. Thus, the constructions described in the prior art are adenoviruses from which the E1 (E1a and/or E1b) and possibly E3 regions have been deleted, in which regions, the heterologous DNA sequences are inserted (Levrero et al., Gene 101 (1991) 195; Gosh-Choudhury et al., Gene 50 (1986) 161). Other constructions contain a deletion in the E1 region and of a non-essential portion of the E4 region (WO94/12649). Nevertheless, the vectors described in the prior art have some drawbacks which limit their use in gene therapy. In particular, the batches of recombinant viruses of the type described in the prior art may be contaminated with replicative particles, in particular of the wild type.

Figure 2A:
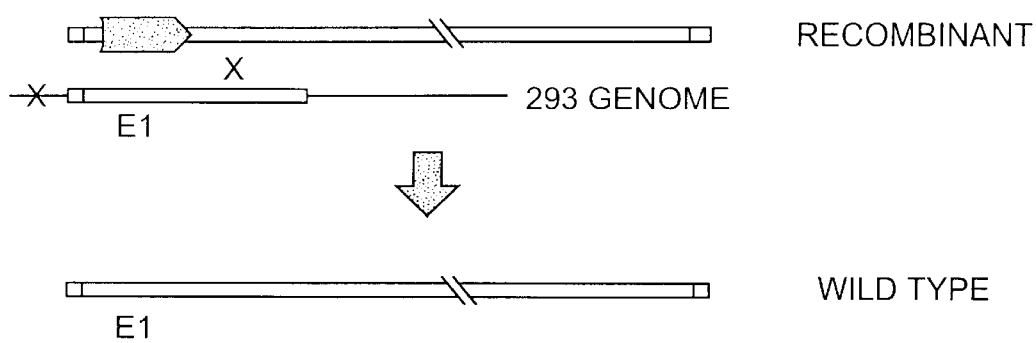
Figure 2B:
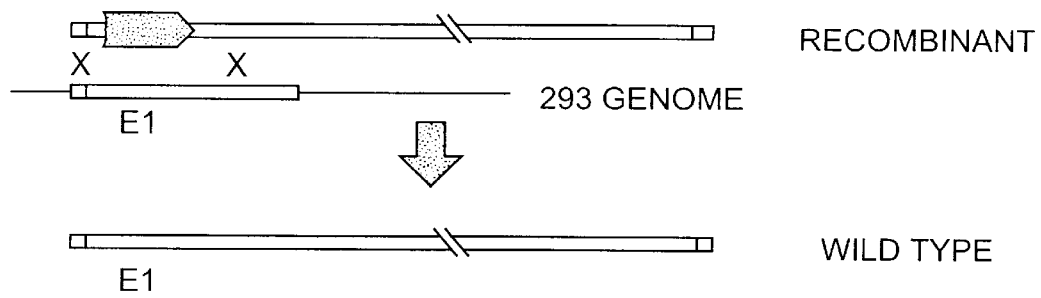

At the present time, the vectors derived from adenoviruses are, in effect, produced in a complementation line (line 293) in which a portion of the adenovirus genome has been integrated. More specifically, line 293 contains the left-hand end (approximately 11–12%) of the adenovirus serotype 5 (Ad5) genome, comprising the left-hand ITR, the encapsidation region and the E1 region, including E1a, E1b and a portion of the region coding for the pIX protein. This line is capable of trans-complementing recombinant adenoviruses which are defective for the E1 region, that is to say lacking all or part of the E1 region, necessary for replication. In effect, E1– recombinant adenoviruses may be prepared in 293 cells as a result of the good trans-complementation of the E1 region contained in this line. Nevertheless, there are zones of homology between the adenovirus region integrated in the genome of the line and the DNA of the recombinant virus which it is desired to produce. As a result, during production, different recombination events may take place, generating replicative viral particles, in particular adenoviruses of the E1+ type. As shown in FIG. 2, the outcome can be a single recombination event followed by chromosome breakage (FIG. 2A), or a double recombination (FIG. 2B). These two types of modification lead to a replacement of the left-hand portion of the recombinant DNA, lacking a functional E1 region, by the corresponding portion present in the genome of the cell, which carries a functional copy of the E1 region. Moreover, in view of the high titres of recombinant vector produced by line 293 (greater than $10^{12}$), the probability of these recombination events taking place is high. In fact, it has been found that many batches of defective recombinant adenoviral vectors were contaminated with replicative viral particles.

Contamination with replicative particles constitutes a major drawback. In effect, the presence of such particles in therapeutic compositions would induce in vivo a viral propagation and an uncontrolled dissemination, with risks of an inflammatory reaction, of recombination, and the like. Hence the contaminated batches cannot be used in human therapy.

The present invention enables these drawbacks to be remedied. The present invention describes, in effect, new constructions permitting the production of defective recombinant adenoviruses completely lacking contamination with replicative particles. The present invention also describes a method for the production of these recombinant adenoviruses. It thus provides new defective recombinant vectors derived from adenoviruses which are especially suitable for use in gene therapy, in particular for the transfer and expression of genes in vivo.

The present invention lies more especially in the construction of defective recombinant adenoviruses comprising an adenovirus genome whose genetic organization is modified, and the possible recombination of which with the genome of the producing line leads to the generation of non-replicative and/or non-viable viral particles. The Applicant has now shown that it is possible to modify the genomic organization of the adenovirus in order to avoid the production of replicative particles during the production of the stocks.

A first subject of the present invention hence relates to a recombinant adenovirus comprising an adenovirus genome (i) whose E1 region is inactivated, (ii) whose genomic organization is modified, and (iii) the possible recombination of which with the genome of the producing line leads to the generation of non-viable viral particles.

For the purposes of the present invention, genetic or genomic organization is understood to mean the arrangement of the different genes or functional regions present in the genome of the wild-type adenovirus as shown in FIG. 1. A modified genetic or genomic organization hence corresponds to a genome in which some genes or some regions are not in their original position. Thus, some genes or some regions may be moved from the genome and inserted at another site. It is also possible to insert a given gene or region at a particular site, and to eliminate or inactivate the original region (by mutation, deletion, insertion, and the like).

The term non-viable viral particle denotes, for the purposes of the invention, an adenovirus incapable of replicating its DNA and/or of propagating autonomously in the infected cells. A non-viable viral particle hence possesses an adenovirus genome lacking at least sequences necessary for its replication and/or its propagation in the infected cell. These regions may be either removed (wholly or partially), or rendered non-functional, or substituted by other sequences. The sequences necessary for replication and/or propagation are, for example, the E1 region, the E4 region or the L5 region. More especially, as regards the E4 region, the important genes are the ORF3 and ORF6 genes.

The Applicant has shown, more especially, that it is possible to move a function essential to viral replication or propagation without affecting the properties of the adenovirus as a vector for gene therapy, namely its high power of infection of cells, in particular human cells, and its capacity to transfer a gene of interest effectively to said cells. Thus, in a preferred embodiment, the subject of the present invention is recombinant adenoviruses in which a region essential to viral replication and/or propagation is present in a genomic position other than its original position. Advantageously, this region lies in or in proximity to another genomic region which is rendered non-functional.

The vectors of the invention are especially advantageous, since they enable large genes of interest to be incorporated and can be produced at high titres without the production of any contaminating replicative viral particle.

In the vectors of the invention the E1 region or any other region may be inactivated or rendered non-functional by different techniques known to a person skilled in the art, and in particular by elimination, substitution, deletion and/or addition of one or more bases. Such modifications may be obtained in vitro (on isolated DNA) or in situ, for example by means of genetic engineering techniques or alternatively by treatment by means of mutagenic agents. Said genetic modification or modifications may be localized in a coding portion of the region or outside a coding region, and for example in the regions responsible for the expression and/or transcriptional regulation of said genes. The inactivation may hence manifest itself in the production of proteins which are inactive as a result of structural or conformational modifications, by the absence of production, by the production of proteins having impaired activity or alternatively by the production of natural proteins at a level which is attenuated or according to a desired mode of regulation.

Among the mutagenic agents which can be used for the inactivation, there may be mentioned, for example, physical agents such as energetic radiation (X, γ, ultraviolet rays, and the like), or chemical agents capable of reacting with different functional groups of the DNA bases, and for example alkylating agents [ethyl methanesulphonate (EMS), N-methyl-N'-nitro-N-nitrosoguanidine, N-nitroquinoline 1-oxide (NQO)], bialkylating agents, intercalating agents, and the like.

The genetic modifications may also be obtained by gene disruption, for example according to the protocol initially described by Rothstein [Meth. Enzymol. 101 (1983) 202]. In this case, all or part of the coding sequence is preferably disrupted to permit the replacement, by homologous recombination, of the genomic sequence by a non-functional or mutant sequence.

Preferably, in the adenoviruses of the invention, the region in question is inactivated by mutation and/or deletion of one or more bases. Still more preferably, it is inactivated by total or partial deletion.

More especially, deletion is understood to mean any elimination of all or part of the gene in question. This can apply, in particular, to all or part of the coding region of said gene, and/or of all or part of the transcription promoter region of said gene. The elimination may be performed by digestion by means of suitable restriction enzymes, followed by ligation, according to the standard techniques of molecular biology, as illustrated in the examples.

As a special preference, the inactivation of the genes is carried out in such a way that it affects only the gene in question and not the other viral genes, in particular the neighbouring genes. Moreover, since some modifications such as point mutations are inherently capable of being corrected or attenuated by cellular mechanisms, it is especially preferable for the inactivation to be completely segregationally stable and/or irreversible.

In the case of inactivation by total or partial deletion, the region essential to viral viability preferably lies in or in proximity to the deletion site. It is, however, possible to use other insertion sites, such as, for example, restriction sites already present in the wild-type genome. In this connection, it is nevertheless preferable for the insertion to be carried out at least in proximity to the deletion site, that is to say outside the deletion site, but sufficiently ready for recombination events not to be able to take place in the space separating the deletion site and the insertion site. Preferably, the distance between the deletion site and the insertion site should not exceed 50 bp.

In a preferred embodiment of the present invention, the region essential to viral replication and/or propagation is moved so as to be included in the inactivated E1 region and/or the E3 region.

According to an especially advantageous embodiment, in the recombinant adenoviruses of the present invention, the E1 region is inactivated by deletion of a PvuII-BglII fragment extending from nucleotide 454 to nucleotide 3328 on the Ad5 adenovirus sequence. This sequence is accessible in the literature and also on a database (see, in particular, Genebank No. M73260). In another preferred embodiment, the E1 region is inactivated by deletion of a HinfII-Sau3A fragment extending from nucleotide 382 to nucleotide 3446.

The region essential to viral replication and/or propagation according to the present invention is advantageously chosen from all or part of the E4 region and/or of the pIX-IVa2 region and/or of the L5 region, and the like.

In an especially preferred embodiment of the present invention, the essential region consists of all or a functional portion of the E4 region, and it is inserted in or in proximity to the E1 deletion site. According to this embodiment, the E4 region, essential to viral propagation, is inserted in a position other than its original position, so that this region is absent in any construction which might result from recombination with the genome of the producing line (see FIG. 3). Hence the subject of the present invention is also a recombinant adenovirus whose genome is distinguished by the presence of inactivated E1 and E4 regions, and in which all or a functional portion of the E4 region is inserted in or in proximity to the E1 region.

An adenoviral vector of this kind preferably comprises two ITRs, an encapsidation region, a deletion in the E1 region in which all or a functional portion of E4 is inserted, and an inactivated original E4 region.

Figure 4:
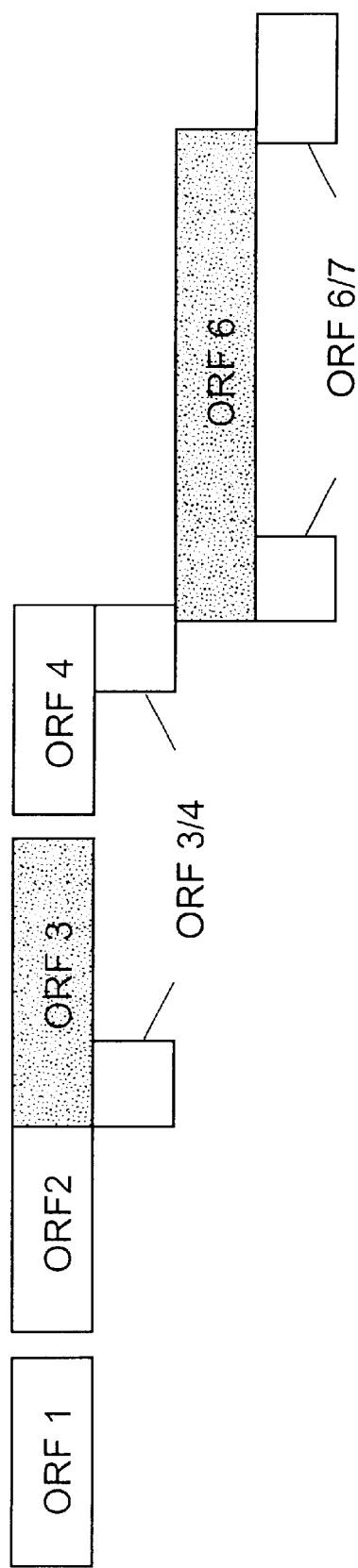

The E4 region is involved in regulation of the expression of the late genes, in the stability of the late nuclear RNAs, in abolition of the expression of the proteins of the host cell and in the efficacy of the replication of the viral DNA. Mutants lacking E4 are incapable of propagating. E4 thus constitutes a region essential to viral replication and/or propagation. This E4 region consists of 7 open reading frames, designated ORF1, ORF2, ORF3, ORF4, ORF3/4, ORF6 and ORF6/7 (FIG. 4). Among these, ORF3 and ORF6 are the two genes essential to viral propagation. Each of these genes is capable of inducing viral propagation. On the other hand, inactivation of the E4 region involves the inactivation of ORF3 and ORF6.

In a particular embodiment, in the vectors of the invention, the whole of the E4 region is inserted in or in proximity to the E1 deletion site. The region can correspond, in particular, to an MaeII-MscI fragment corresponding to nucleotides 35835–32720.

In another particular embodiment, only a functional portion of E4, that is to say a portion sufficient to permit viral propagation, is inserted. This portion comprises at least one functional ORF3 or ORF6 gene. Preferably, the functional portion of E4 consists essentially of ORF3 or ORF6. As an example, these coding frames may be isolated from the E4 region in the form of PvuII-AluI and BglII-PvuII fragments, respectively, corresponding to nucleotides 34801–34329 and 34115–33126, respectively.

Advantageously, the E4 region or the functional portion of this region also comprises a transcription promoter region. The promoter in question can be that of the E4 region or any other functional promoter, such as viral (E1a, SV40, RSV LTR, and the like), eukaryotic or mammalian promoters. Preferably, the promoter used is the promoter of the E4 region.

As mentioned above, the functional portion of E4 inserted in E1 does not necessarily correspond to the portion of E4 deleted in the original position. Thus, the initial region may be inactivated by point mutation (without deletion), and a functional E4 region inserted in E1. Likewise, the initial E4 region may be completely deleted, and only a functional portion inserted in E1.

Inactivation of the E4 region implies, for the purposes of the invention, the functional inactivation of at least the ORF3 and ORF6 regions. These original regions may be inactivated by any technique known to a person skilled in the art. In particular, all the methods given above may be applied to the inactivation of ORF3 and ORF6 or any additional region of E4. As an example, deletion of the E4 region of the virus Ad2 dl808 or of the viruses Ad5 dl1004, Ad5 dl1007, Ad5 dl1011 or Ad5 dl1014 may be used in the context of the invention (see Example 3).

These adenoviruses may be obtained, for example, by cotransfection into a producing line of a first plasmid carrying the left-hand portion of the genome of the virus which it is desired to produce (possessing a deletion in the E1 region in or in proximity to which at least a functional portion of E4 is inserted), and a viral genomic DNA fragment supplying the right-hand portion of the genome of the virus (possessing an inactivated E4 region). After recombination, the viruses produced are amplified and isolated. These adenoviruses may also be obtained by interchanging the ends of the genome, comprising the ITRs plus the adjacent region. In this connection, the subject of the invention is also a recombinant adenovirus whose genome possesses an inactivated E1 region, and in which the left-hand end, comprising the ITR and the encapsidation region, and the right-hand end, comprising the ITR and all or a functional portion of the E4 region, are interchanged. More especially, the left-hand end comprising the left-hand ITR and the encapsidation region is contained in the first 382 nucleotides of the Ad5 adenovirus genome (for example up to the HinfI site). Likewise, the right-hand end comprising the right-hand ITR and all or a functional portion of the E4 region, including the promoter of the E4 region, is contained in the last 3215 nucleotides of the Ad5 adenovirus genome (for example from the MscI site at position 32720). The techniques of a person skilled in the art enable a recombinant virus according to the invention to be constructed in which the right-hand ITR and all or part of the E4 region are now located on the left-hand side of the virus, followed by the region 3446–32720 of the Ad5 adenovirus genome, then the encapsidation sequence and the left-hand ITR which now becomes the right-hand end of the recombinant virus (see FIG. 5). The genome of the recombinant adenovirus thereby obtained is especially advantageous, since the essential E4 region moved to the left is maintained in its natural environment and hence under optimal conditions of activity for a high-titre infectious cycle. Furthermore, this region now precedes the region whose presence in the genome of the producing line 293 was the source of the appearance of viable particles.

Figure 6:
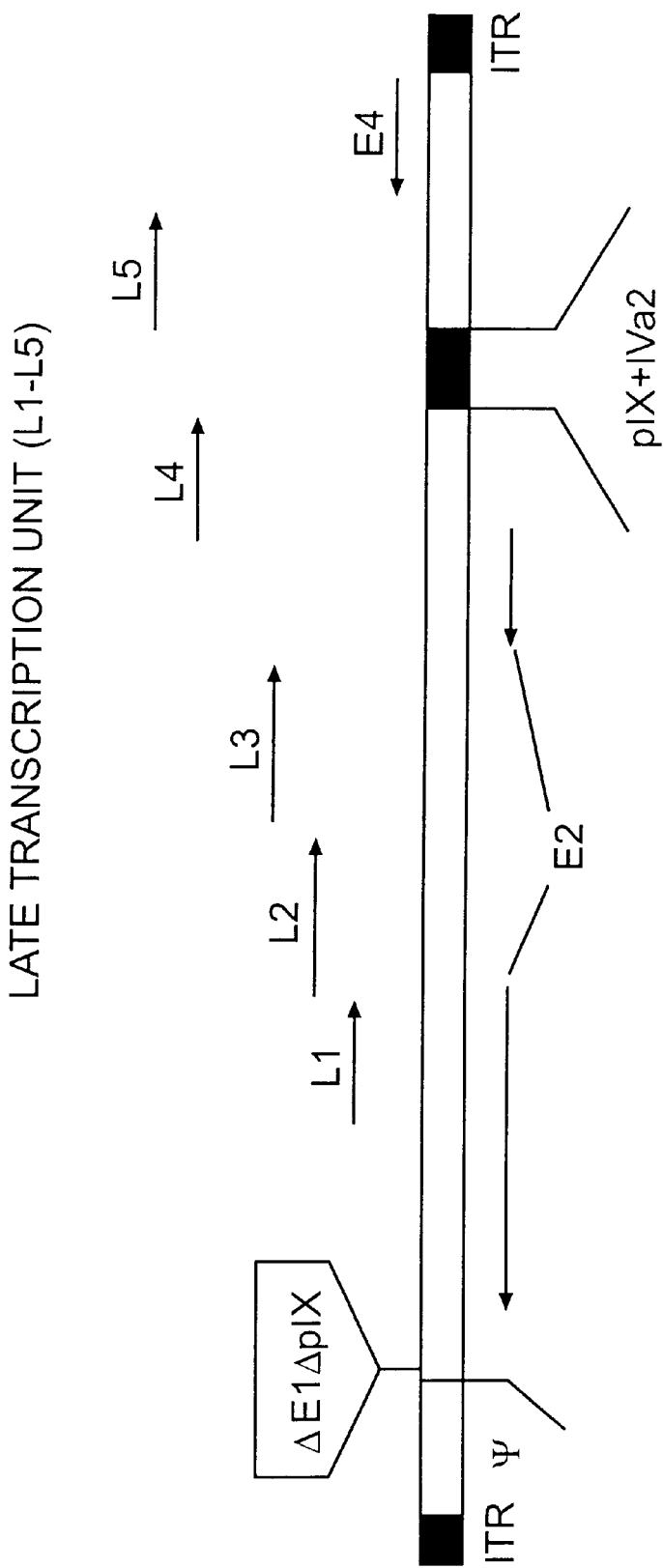

In another, most especially preferred embodiment of the present invention, the essential region consists of the region coding for the pIX and IVa2 proteins, and it is inserted in the E3 region, optionally as a replacement for deleted sequences (see FIG. 6). More especially, the region coding for the pIX and IVa2 proteins is included in a BglII-NruI fragment corresponding to nucleotides 3328 to 6316 on the wild-type Ad5 adenovirus sequence. In this embodiment, the possible recombination of the recombinant adenovirus with the adenovirus region integrated in the producing line generates only nonviable viral particles, since the main late genes essential to viability have been deleted from them.

According to a particular embodiment of the invention, two essential regions of the adenovirus genome are moved from their original positions. More preferably, these essential regions are represented by the region coding for the pIX protein and the region coding for all or only a functional portion of the E4 region. According to a preferred embodiment, they will be moved to the E1 region, as a replacement for deleted sequences and preserving or otherwise the orientation of their reading frame.

Figure 8:
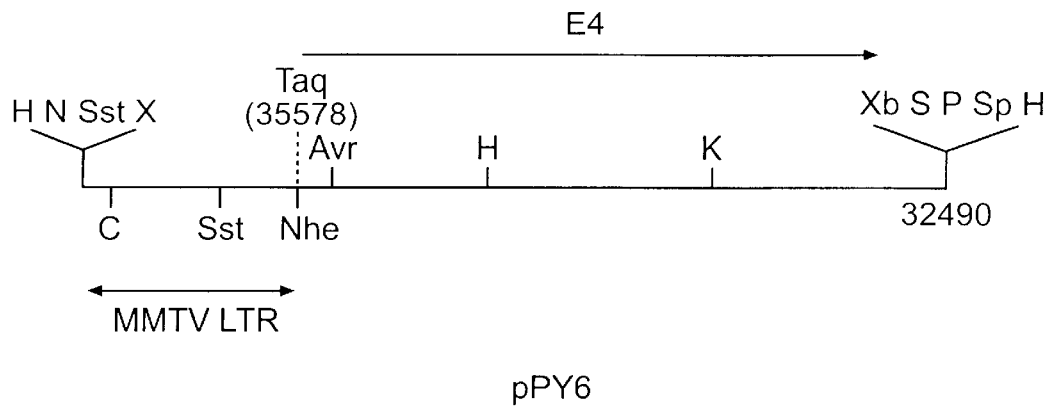
Figure 8:
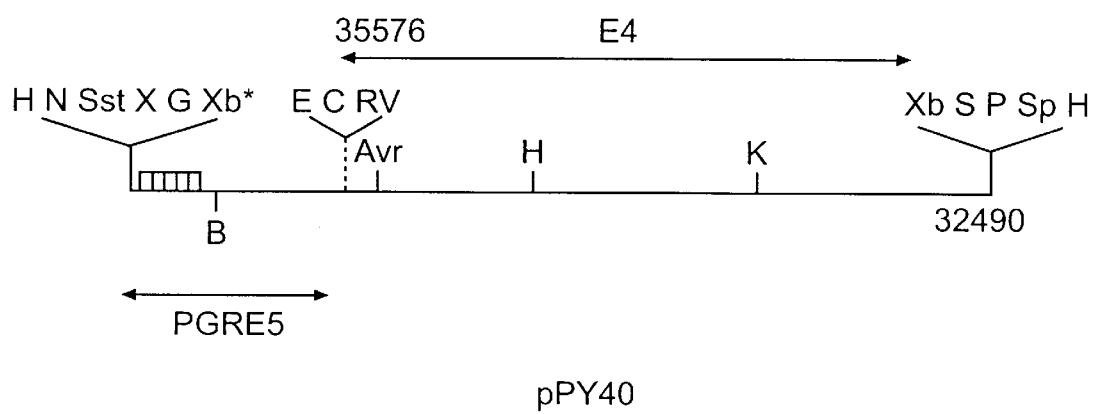

By way of illustration of this type of construction, reference may be made more especially to the construction shown in FIG. 8. In this construction, the region coding for the pIX protein is moved into the deleted E1 region, on the right-hand side of the left-hand ITR which has become, right-hand end of the recombinant virus. The region coding for the pIX protein is, in addition, placed therein reading in the reverse direction. As regards the essential region of E4, this is represented therein by the ORF3-ORF6/7 genes under the control of the E4 promoter, and is also inserted therein in the E1 deletion site, between the region coding for the pIX protein and the region coding for the IVa2 protein, whose position has not been affected; in the case of the specific construction of FIG. 8, the two regions coding for the pIX protein and the IVa2 protein, respectively, possess separate polyadenylation sites.

A construction of this kind is especially advantageous from the standpoint of reliability and safety. In effect, any spurious recombination between 2 viral molecules of this type, in the E4 region for example, will lead to a recombinant virus bereft of its encapsidation sequence. Likewise, a recombination between a viral molecule of this kind with the complementary region of said adenovirus, the region being integrated in a producing cell line, will generate only viral particles from which their main late genes essential to their viability have been deleted.

As mentioned above, the recombinant adenoviruses according to the invention advantageously comprise the ITR sequences and a region permitting encapsidation.

The inverted repeat sequences (ITR) constitute the origin of replication of the adenoviruses. They are localized at the 3' and 5' ends of the viral genome (see FIG. 1), from where they may be readily isolated according to the standard techniques of molecular biology known to a person skilled in the art. The nucleotide sequence of the ITR sequences of human adenoviruses (especially of the serotypes Ad2 and Ad5) is described in the literature, as well as those of canine adenoviruses (in particular CAV1 and CAV2). As regards the Ad5 adenovirus for example, the left-hand ITR sequence corresponds to the region comprising nucleotides 1 to 103 of the genome.

The encapsidation sequence (also designated Psi sequence) is needed for encapsidation of the viral genome. This region must hence be present in order to permit the preparation of defective recombinant adenoviruses according to the invention. The encapsidation sequence is localized in the genome of the wild-type adenoviruses, between the left-hand ITR and the E1 gene (see FIG. 1). In the adenoviruses of the invention, it may be localized next to either the left-hand ITR or the right-hand ITR (see FIG. 5). It may be isolated or synthesized artificially by the standard techniques of molecular biology. The nucleotide sequence of the encapsidation sequence of human adenoviruses (especially of the serotypes Ad2 and Ad5) is described in the literature, as well as those of canine adenoviruses (in particular CAV1 and CAV2). As regards the Ad5 adenovirus for example, a functional encapsidation sequence lies between nucleotides 194 and 358 of the genome.

Moreover, the adenoviruses according to the invention can possess other modifications in respect of their genome. In particular, other region may be deleted in order to increase the capacity of the virus and to reduce these side effects associated with the expression of viral genes. Thus, all or part of the E3 region in particular may be deleted.

Recombinant adenoviruses according to the invention possess especially attractive properties for use in gene therapy. These vectors combine, in effect, very high infection, safety and gene transfer capacity properties.

Advantageously, the recombinant adenoviruses of the invention contain, in addition, a heterologous nucleic acid sequence whose transfer to a cell, organ or organism and/or expression therein is/are sought.

In particular, the heterologous DNA sequence can contain one or more therapeutic genes. The therapeutic genes which can thus be transferred are any gene whose transcription and, where appropriate, translation in the target cell generate products having a therapeutic effect.

The genes in question can, in particular, be ones coding for proteinaceous products having a therapeutic effect. The proteinaceous product thus encoded can be a protein, a peptide, an amino acid, and the like. This proteinaceous product can be homologous with respect to the target cell (that is to say a product which is normally expressed in the target cell when the latter does not display any pathology). In this case, the expression of a protein makes it possible, for example, to compensate for an insufficient expression in the cell or for the expression of a protein that is inactive or poorly active as a result of a modification, or alternatively to overexpress said protein. The therapeutic gene can also code for a mutant of a cellular protein, having enhanced stability, modified activity, and the like. The proteinaceous product can also be heterologous with respect to the target cell. In this case, an expressed protein can, for example, supplement or supply an activity which is deficient in the cell, enabling it to combat a pathology.

Among the products which are therapeutic for the purposes of the present invention, there may be mentioned, more especially, enzymes, blood derivatives, hormones, lymphokines, namely interleukins, interferons, TNF, and the like (FR 92/03120), growth factors, neuro-transmitters or their precursors or synthetic enzymes, trophic factors, namely BDNF, CNTF, NGF, IGF, GMF, aFGF, bFGF, NT3, NT5, and the like; apolipoproteins, namely ApoAI, ApoAIV, ApoE, and the like (FR 93/05125), dystrophin or a minidystrophin (FR 91/11947), tumor-suppressing genes, namely p53, Rb, Rap1A, DCC, k-rev, and the like (FR 93/04745), genes coding for factors involved in coagulation, namely factors VII, VIII, IX, and the like, suicide genes, namely those for thymidine kinase, cytosine desaminase, and the like; or alternatively all or part of a natural or artificial immunoglobulin (Fab, ScFv, and the like), and the like.

The therapeutic gene can also be an antisense gene or sequence, the expression of which in the target cell enables the expression of cellular genes or the transcription of cellular mRNA to be controlled. Such sequences can, for example, be transcribed in the target cell into RNAs complementary to cellular mRNAs, and can thus block their translation into protein, according to the technique described in Patent EP 140,308.

The therapeutic gene can can also be a gene coding for an antigenic peptide capable of generating an immune response in humans. In this particular embodiment, the invention hence makes it possible to produce vaccines enabling humans to be immunized, in particular against microorganisms or viruses. Such antigenic peptides can be, in particular, ones specific to the Epstein-Barr virus, the HII virus, the hepatitis B virus (EP 185,573) or the pseudorabies virus, or alternatively tumor-specific (EP 259,212).

Generally, the heterologous nucleic acid sequence also comprises a transcription promoter region which is functional in the infected cell, as well as a region located on the 3' side of the gene of interest, and which specifies a transcription termination signal and a polyadenylation site. This set of elements constitutes the expression cassette. As regards the promoter region, this can be a promoter region which is naturally responsible for the expression of the gene in question when the region is capable of functioning in the. infected cell. The promoter regions can also be ones of different origin (responsible for the expression of other proteins, or even synthetic regions). In particular, they can be promoter sequences of eukaryotic or viral genes. For example, they can be promoter sequences originating from the genome of the cell which it is desired to infect. Likewise, they can be promoter sequences originating from the genome of a virus, including the adenovirus used. In this connection, the promoters of the E1A, MLP (major late promoter), CMV (cytomegalovirus), RSV (Rous sarcoma virus), and the like, genes may be mentioned for example. In addition, these promoter regions may be modified by the addition of activator or regulatory sequences, or sequences permitting a tissue-specific or -preponderant expression. Moreover, when the heterologous nucleic acid does not contain promoter sequences, it may be inserted into the genome of the defective virus downstream of such a sequence.

Moreover, the heterologous nucleic acid sequence can also contain, especially upstream of the therapeutic gene, a signal sequence directing the synthesized therapeutic product into the pathways of secretion of the target cell. This signal sequence can be the natural signal sequence of the therapeutic product, but it can also be any other functional signal sequence, or an artificial signal sequence.

The cassette for expression of the therapeutic gene may be inserted at different sites of the genome of the recombinant adenovirus according to the invention. It may, in the first place, be inserted at the site of the E1 deletion. In this case, it is localized next to (on the 5' or 3' side) the region or the functional portion of E4. It may also be inserted in the E3 region, in addition to or as a substitute for sequences. It may also be localized in the inactivated E4 region.

Still in an especially advantageous embodiment, the vectors of the invention possess, in addition, a functional E3 gene under the control of a heterologous promoter. More preferably, the vectors possess a portion of the E3 gene permitting expression of the gp19K protein. This protein makes it possible, in effect, to prevent the adenovirus vector from becoming the subject of an immune reaction which (i) would limit its action and (ii) might have undesirable side effects.

The recombinant adenoviruses according to the invention may be of diverse origins. There are, in effect, different serotypes of adenovirus, the structure and properties of which vary somewhat but which display a comparable genetic organization. As a result, the teachings described in the present application may be readily reproduced by a person skilled in the art for any type of adenovirus.

More especially, the adenoviruses of the invention may be of human, animal or mixed (human and animal) origin.

As regards adenoviruses of human origin, it is preferable to use those classified in group C. More preferably, among the different serotypes of human adenovirus, it is preferable to use adenoviruses type 2 or 5 (Ad2 or Ad5) in the context of the present invention.

As mentioned above, the adenoviruses of the invention may also be of animal origin, or may contain sequences originating from adenoviruses of animal origin. The Applicant has, in effect, shown that adenoviruses of animal origin are capable of infecting human cells with great efficacy, and that they are incapable of propagating in the human cells in which they have been tested (see Application FR 93/05954). The Applicant has also shown that adenoviruses of animal origin are in no way trans-complemented by adenoviruses of human origin, thereby eliminating any risk of recombination and propagation in vivo in the presence of a human adenovirus, which can lead to the formation of an infectious particle. The use of adenoviruses or of regions of adenoviruses of animal origin is hence especially advantageous, since the risks inherent in the use of viruses as vectors in gene therapy are even lower.

The adenoviruses of animal origin which may be used in the context of the present invention can be of canine, bovine, murine (for example: Mav1, Beard et al., Virology 75 (1990) 81), ovine, porcine, avian or alternatively simian (for example: SAV) origin. More especially, among avian adenoviruses, there may be mentioned the serotypes 1 to 10 which are available in the ATCC, such as, for example, the strains Phelps (ATCC VR-432), Fontes (ATCC VR-280), P7-A (ATCC VR-827), IBH-2A (ATCC VR-828), J2-A (ATCC VR-829), T8-A (ATCC VR-830), K-11 (ATCC VR-921) or alternatively the strains referenced ATCC VR-831 to 835. Among bovine adenoviruses, the different known serotypes may be used, and in particular those available in the ATCC (types 1 to 8) under the references ATCC VR-313, 314, 639–642, 768 and 769. There may also be mentioned murine adenoviruses FL (ATCC VR-550) and E20308 (ATCC VR-528), ovine adenovirus type —5 (ATCC VR-1343) or type 6 (ATCC VR-1340), porcine adenovirus 5359, or simian adenoviruses such as, in particular, the adenoviruses referenced in the ATCC under the numers VR-591–594, 941–943, 195–203, and the like.

Among the different adenoviruses of animal origin, it is preferable in the context of the invention to use adenoviruses or regions of adenoviruses of canine origin, and in particular all strains of CAV2 adenoviruses [strain Manhattan or A26/61 (ATCC VR-800) for example] . Canine adenoviruses have been subjected to many structural studies. Thus, complete restriction maps of CAV1 and CAV2 adenoviruses have been described in the prior art (Spibey et al., J. Gen. Virol. 70 (1989) 165), and the E1a and E3 genes as well as the ITR sequences have been cloned and sequenced (see, in particular, Spibey et al., Virus Res. 14 (1989) 241; Linne, Virus Res. 23 (1992) 119, WO 91/11525).

The defective recombinant adenoviruses according to the invention may be prepared in different ways.

A first method consists in transfecting the DNA of the (defective) recombinant virus prepared in vitro into a competent cell line, that is to say one carrying in trans all the functions necessary for complementation of the defective virus. These functions are preferably integrated in the genome of the cell, thereby reducing the risks of recombination and endowing the cell line with enhanced stability. In the case of adenoviruses in which only the E1 region is deficient, the preferred line is line 293.

A second approach consists in cotransfecting the DNA of the defective recombinant virus prepared in vitro and the DNA of one or more helper viruses or plasmid into a suitable cell line. According to this method, it is not necessary to have at one's disposal a competent cell line capable of complementing all the defective functions of the recombinant adenovirus. A part of these functions is, in effect, complemented by the helper virus or viruses. This/these helper virus(es) are themselves defective. The preparation of defective recombinant adenoviruses of the invention according to this method is also illustrated in the examples.

In this connection, the present application also describes construction of plasmids carrying the modified left-hand portion of the Ad5 adenovirus genome (plasmids of the pCO1-E4 series, for example). These plasmids are especially useful for the construction of recombinant adenoviruses as vectors for gene therapy. Thus, the pCO1-E4 plasmids carry the left-hand region of the adenovirus genome, from the left-hand ITR to nucleotide 6316, with a deletion of the region lying between nucleotides 382 and 3446, corresponding to the E1 locus, in which region all or a functional portion of E4 is inserted. The pCO1-E4 plasmids contain, moreover, a multiple cloning site permitting the incorporation of a heterologous nucleic acid sequence of interest. The pCO1-E4 plasmids may be used to prepare the defective recombinant adenovirus by cotransfection with a DNA, preferably of viral origin, corresponding to the right-hand portion of the genome of the adenovirus possessing an inactivated E4 region, in a competent cell line. As regards the latter DNA, it may originate from the genome of a defective virus such as Ad2 dl808 from which the E4 region has been deleted (Weinberg et al., J. Virol. 57 (1986) 833), AdS dl1004, AdS dl1007, Ad5 dl1011 or Ad50 dl1014, and the like (see examples). In this connection, the invention also relates to a method for preparing recombinant adenoviruses lacking replicative particles, according to which a competent cell line is cotransfected with a first DNA comprising the left-hand portion of the genome of said adenovirus, possessing a deletion in the E1 region in or in proximity to which at least a functional portion of the E4 region is inserted, and a second DNA comprising at least the right-hand portion of the genome of said adenovirus, possessing an inactivated E4 region, and a portion of adenovirus in common with the first DNA, and the adenoviruses produced by homologous recombination between said DNAs are recovered.

Among the cell lines which can be used, the human embryonic kidney line 293 (Graham et al., J. Gen. Virol. 36 (1977) 59) may be mentioned in particular. As stated above, this line contains, in particular, integrated in its genome, the left-hand portion of the Ad5 human adenovirus genome (12%). Advantageously, in the method of the invention, the first DNA is chosen from plasmids of the pCO1-E4 type.

Moreover, in order to prepare a recombinant adenovirus comprising a therapeutic gene, the first or the second DNA employed in the method of the invention carries, in addition, a heterologous DNA sequence of interest.

Thereafter, the recombinant viruses which have multiplied are recovered, purified and amplified according to the standard techniques of virology.

The pCO1-E4 plasmids thus enable recombinant adenoviruses to be constructed carrying a deletion in the E1 region extending from nucleotide 382 to nucleotide 3446, in which region all or a functional portion of E4 is inserted, as well as, where appropriate, a therapeutic gene.

The present invention also relates to any pharmaceutical composition comprising one or more defective recombinant adenoviruses as are described above. The pharmaceutical compositions of the invention may be formulated with a view to topical, oral, parenteral, intranasal, intravenous, intramuscular, subcutaneous, intraocular, transdermal, and the like, administration.

Preferably, the pharmaceutical composition contains vehicles which are pharmaceutically acceptable for an injectable formulation. These can be, in particular, sterile, isotonic saline solutions (monosodium or disodium phosphate, sodium, potassium, calcium or magnesium chloride, and the like, or mixtures of such salts), or dry, in particular lyophilized, compositions which, on adding sterilized water or physiological saline, as the case may be, enable injectable solutions to be formed.

The doses of virus used for the injection may be adapted in accordance with different parameters, and in particular in accordance with the mode of administration used, the pathology in question, the gene to be expressed or the desired period of treatment. Generally speaking, the recombinant adenoviruses according to the invention are formulated and administered in the form of doses of between $10^4$ and $10^{14}$ pfu, and preferably $10^6$ to $10^{10}$ pfu. The term pfu (plaque forming unit) corresponds to the infectious power of a solution of virus, and is determined by infecting a suitable cell culture and measuring, generally after 15 days, the number of plaques of infected cells. The techniques of determination of the pfu titre of a viral solution are well documented in the literature.

Depending on the heterologous DNA sequence inserted, the adenoviruses of the invention may be used for the treatment or prevention of many pathologies, including genetic diseases (dystrophy, cystic fibrosis, and the like), neurodegenerative diseases (Alzheimer's, Parkinson's, ALS, and the like), cancers, pathologies associated with disorders of coagulation or with dyslipoproteinaemias, pathologies associated with viral infections (hepatitis, AIDS, and the like), and the like.

The present invention will be described more completely by means of the examples which follow, which should be considered to be illustrative and non-limiting.

LEGENDS TO THE FIGURES

FIG. 1: Genetic organization of the Ad5 adenovirus. The complete sequence of Ad5 is available on a database, and enables a person skilled in the art to select or create any restriction site, and thus to isolate any region of the genome.

FIG. 2: Single (FIG. 2A) or double (FIG. 2B) recombination events between the adenovirus and line 293.

Figure 3:
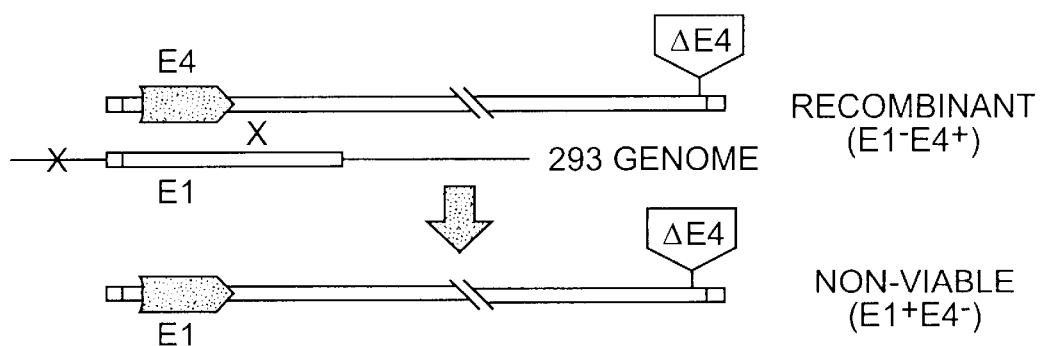
Figure 3:
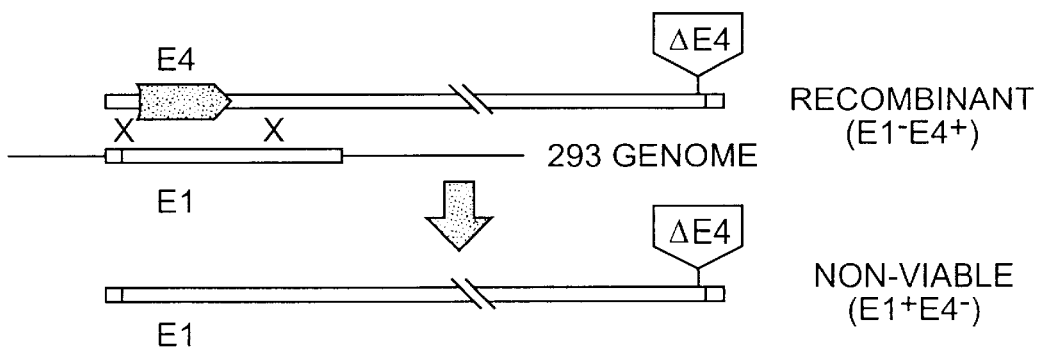

FIG. 3: Diagram of a type of vectors of the invention, and of its recombination with line 293.

FIG. 4: Organization of the E4 region.

Figure 5:
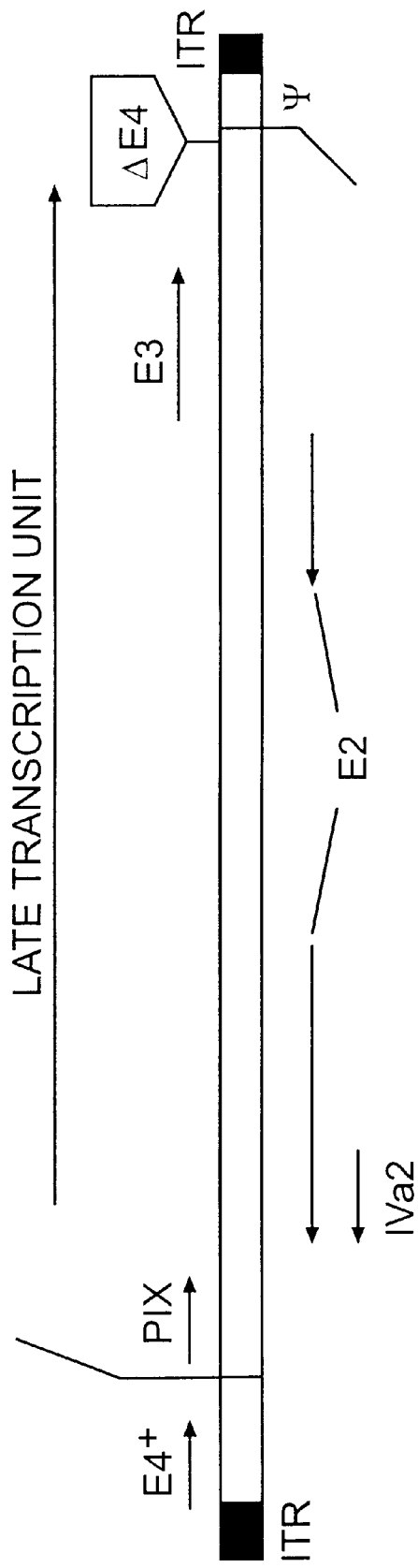

FIG. 5: Diagram of an adenovirus of the invention having interchanged ends. E4+ denotes a functional E4 region; ΔE4 denotes a non-functional E4 region, ψ denotes an encapsidation sequence. The cassette for expression of the gene of interest is not shown, but may be inserted as indicated in the text.

FIG. 6: Diagram of a type of vectors of the invention (pIX-IVa2). pIX+IVa2 contains at least one functional IVa2 region. ΔE1ΔpIX denotes a deletion of the adenovirus sequences lying between the ψ region and the end of the region coding for the 140 kD protein (position 5200) of the E2 region. This deletion also includes the IVa2 region and affects the sequence present in the line 293 chromosome downstream of the E&b region.

Figure 7:
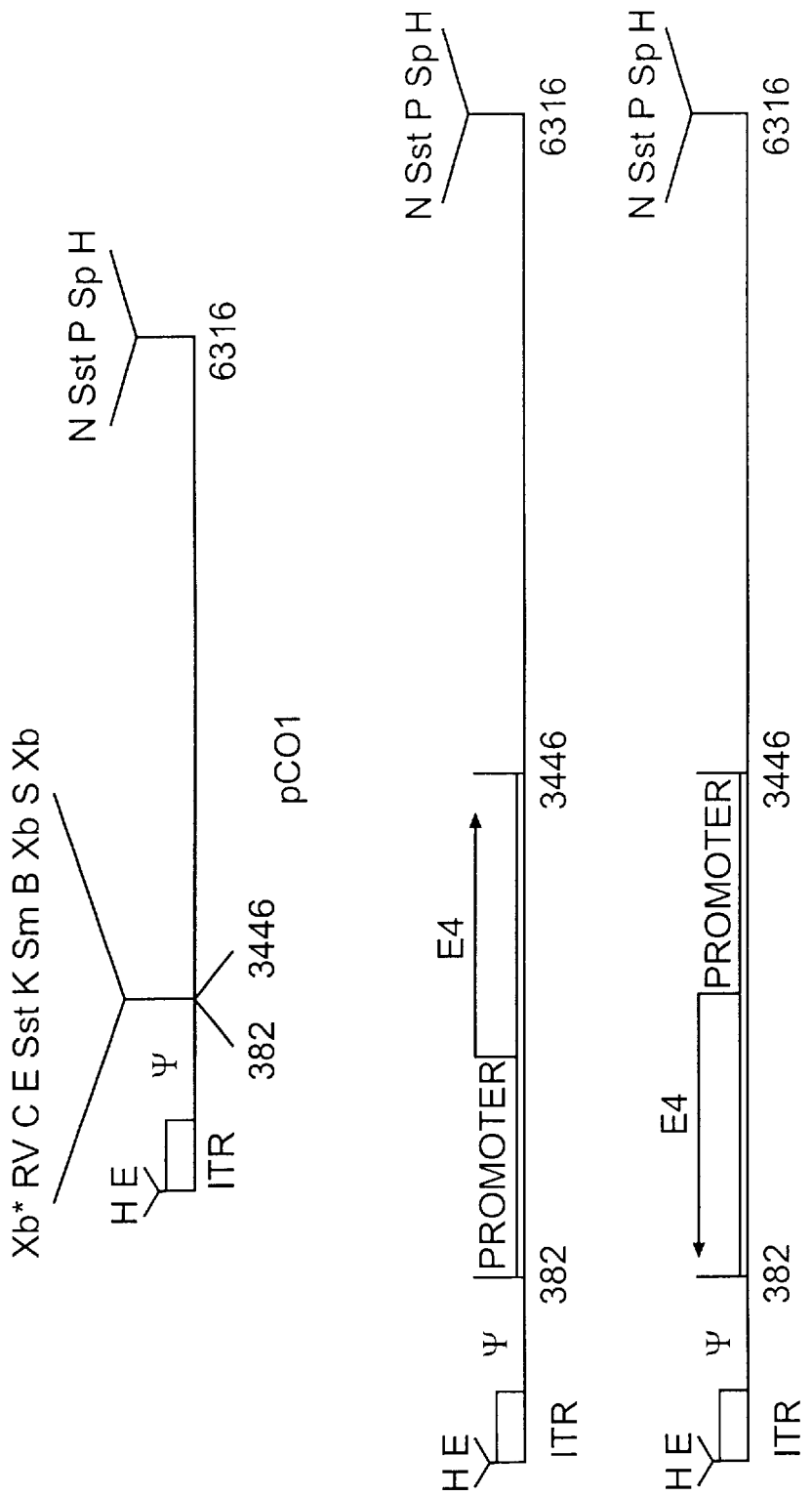

FIG. 7: Restriction map of the HindIII fragment contained in the plasmid pCO1.

FIG. 8: Diagram of the expression plasmids pPY40 and pPY6.

Figure 9:
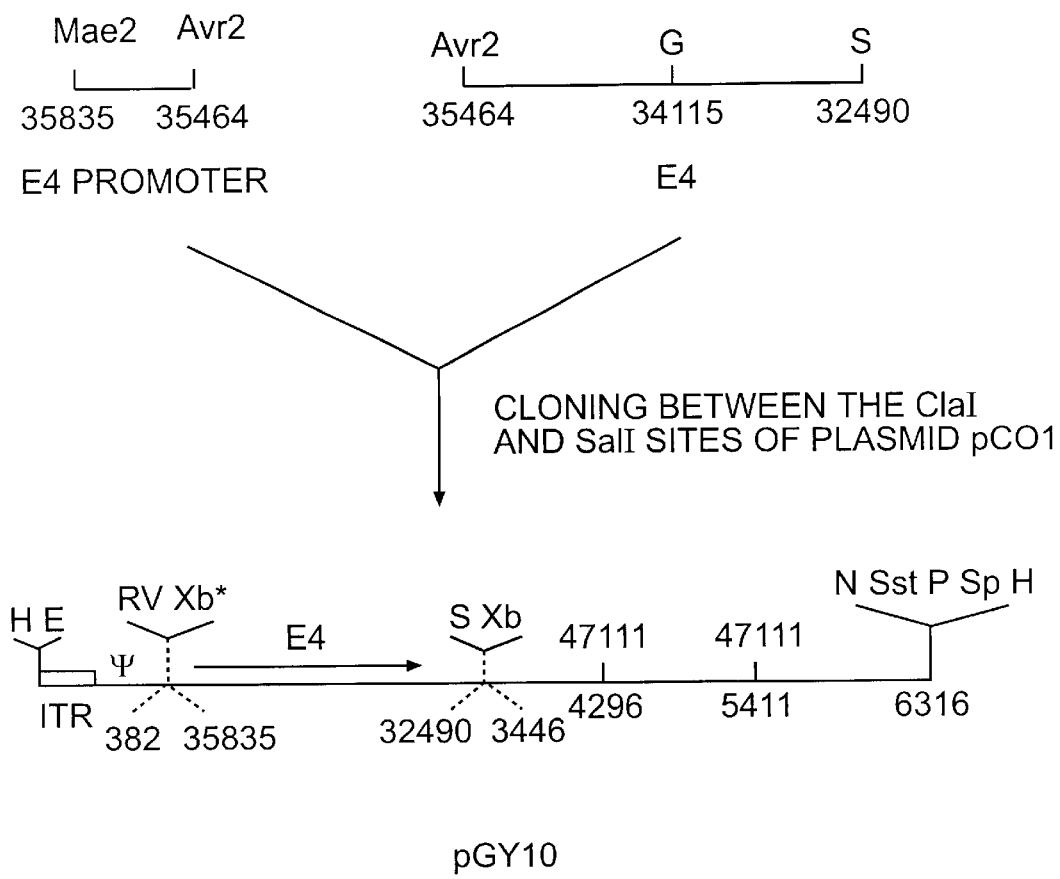

FIG. 9: Diagram of the plasmid pGY10.

Figure 10:
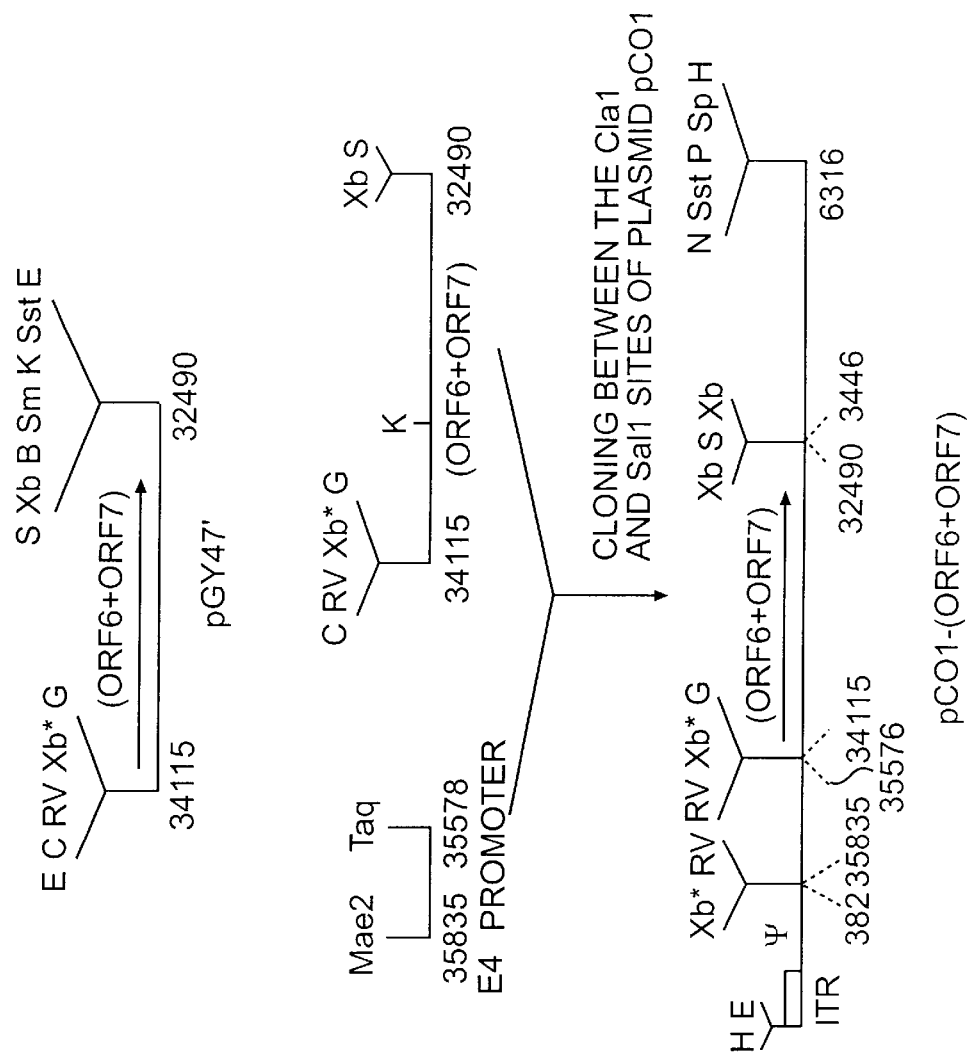

FIG. 10: Diagram of the plasmid pCO1-(ORF6+ORF7).

Figure 11:
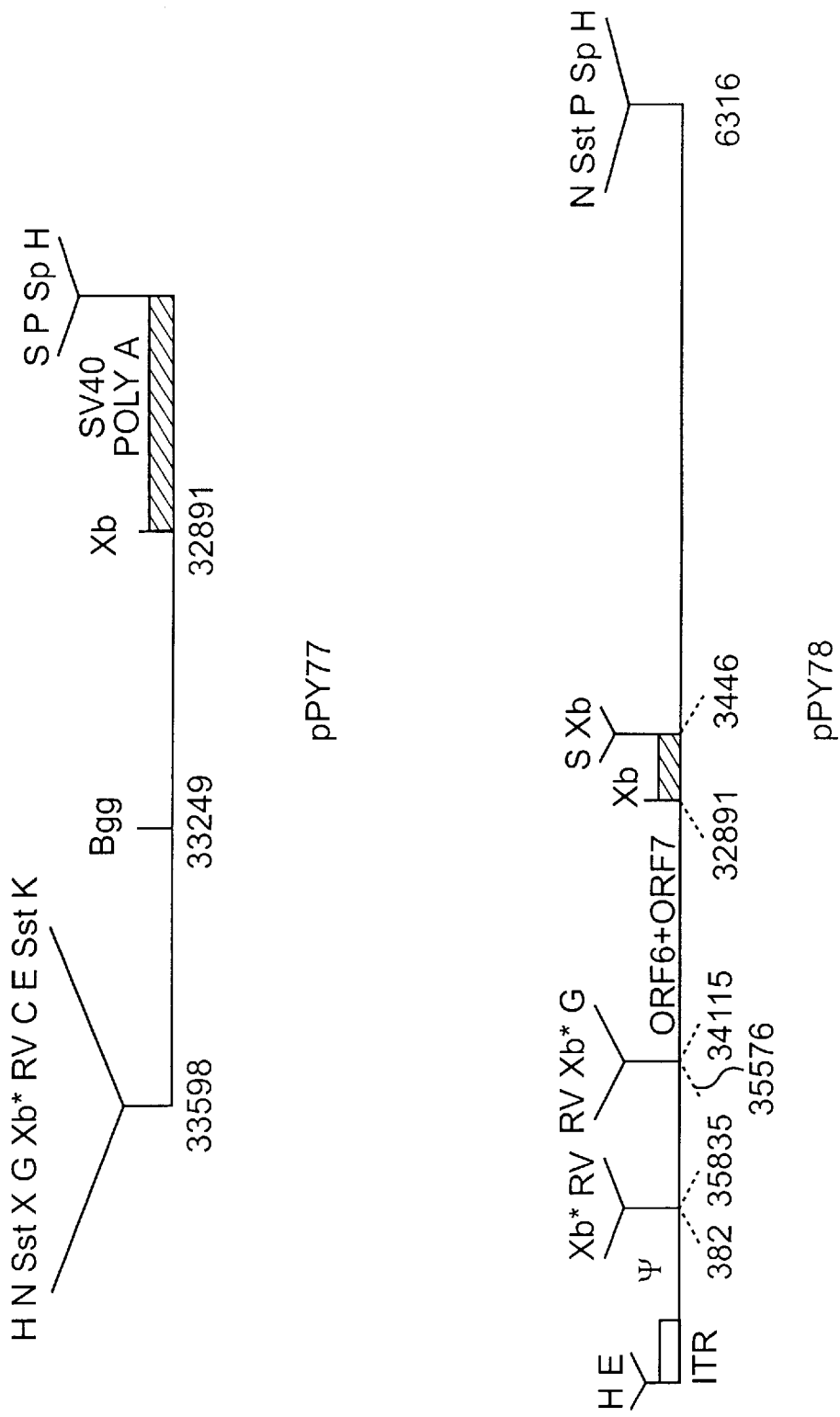

FIG. 11: Diagram of the plasmids pPY78 and pPY77.

Figure 12:
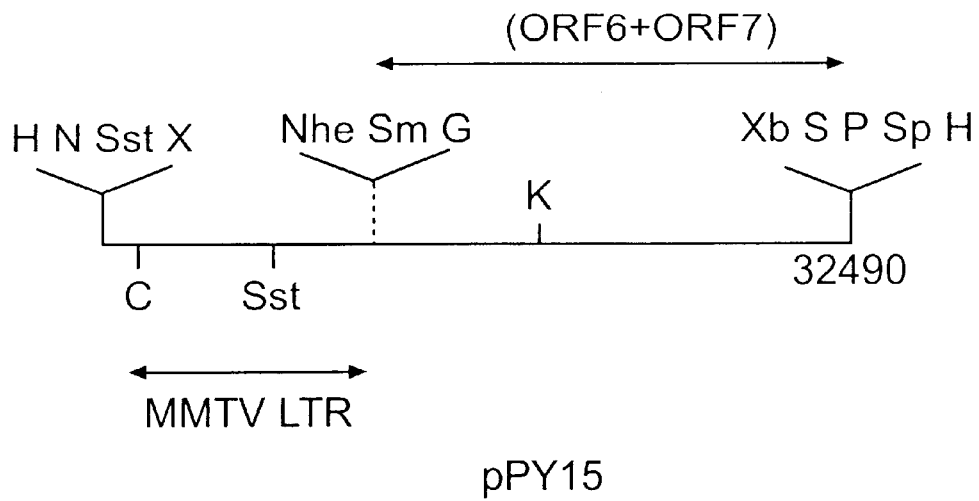
Figure 12:
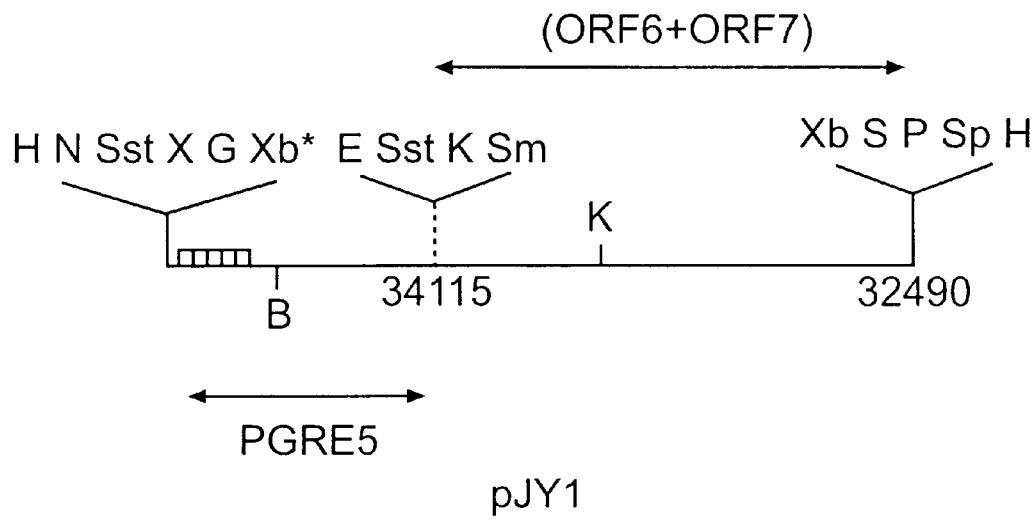

FIG. 12: Diagram of the plasmids pPY15 and pJY1.

Figure 13:
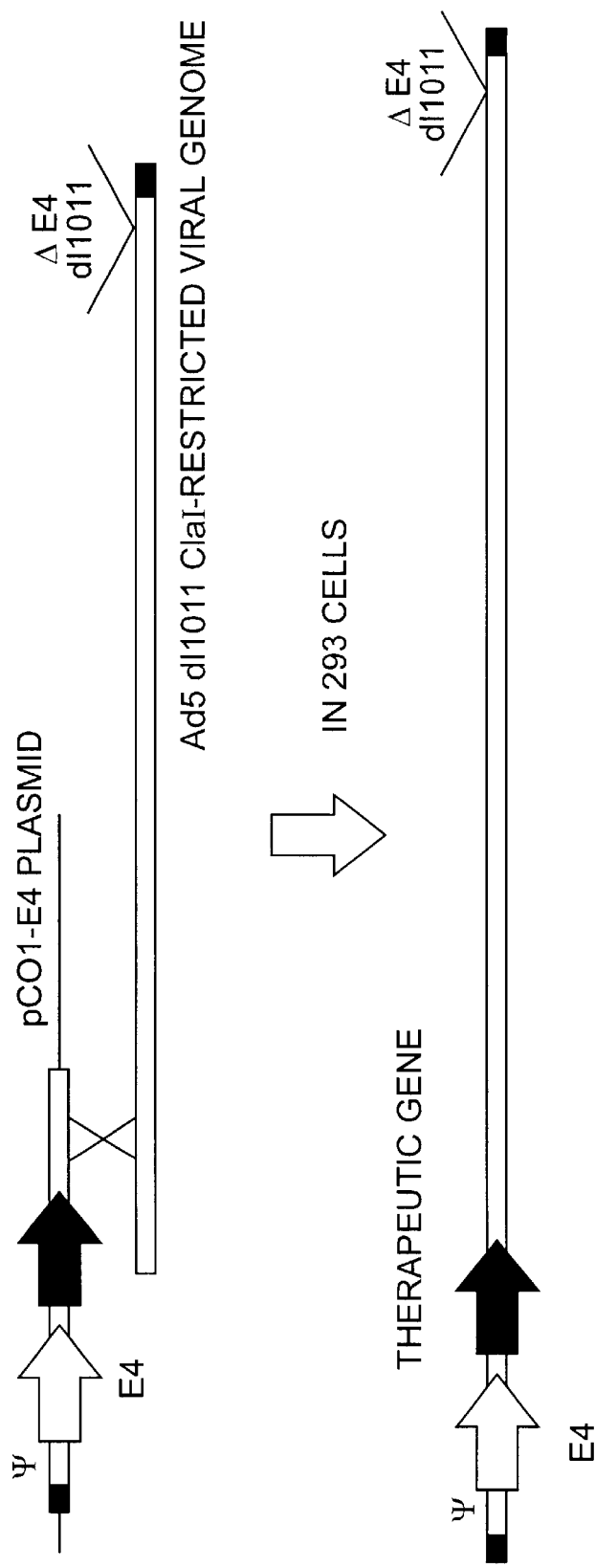

FIG. 13: Diagram of a type of virus according to the invention.

Figure 14:
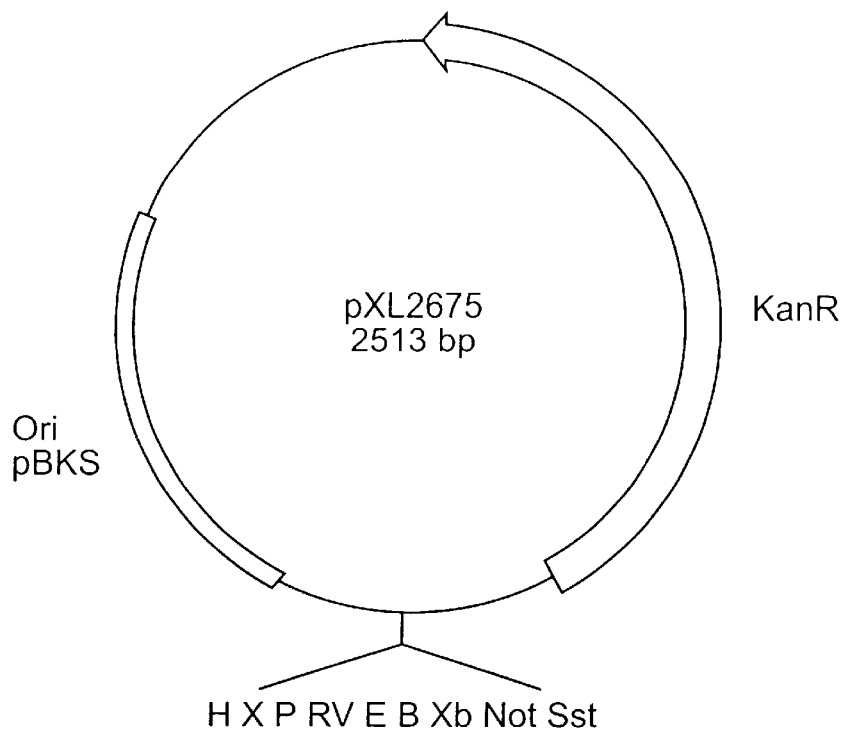
Figure 14:
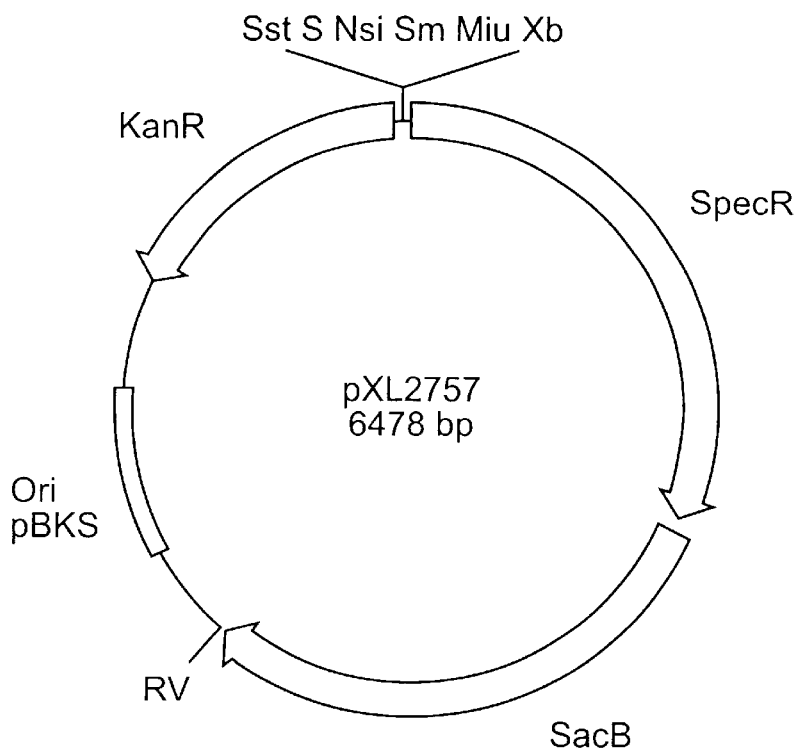

FIG. 14: Diagram of the plasmids pXL2675 and pXL2757.

Figure 15:
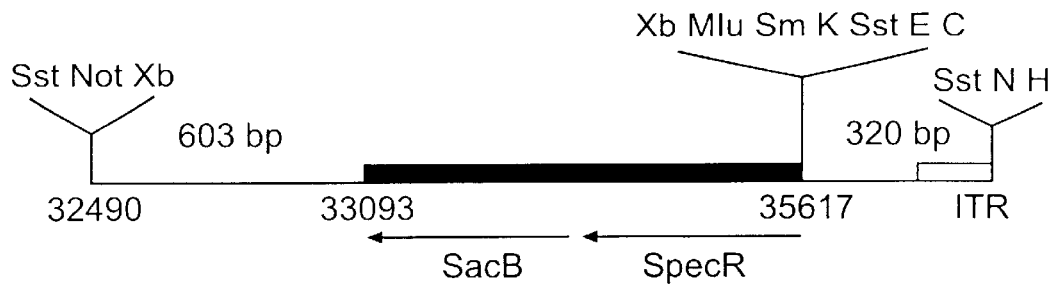
Figure 15:
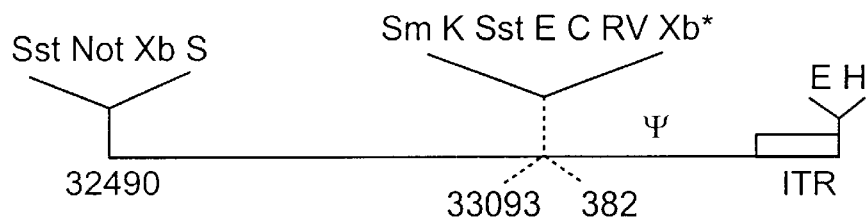
Figure 15:
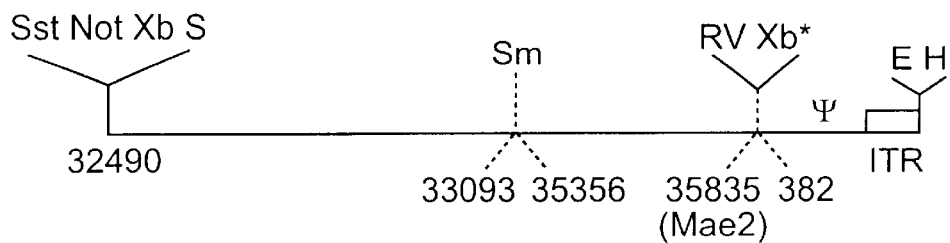

FIG. 15: Diagram of the restriction maps of the plasmids pPY66, pPY82 and pPY75.

Figure 16:
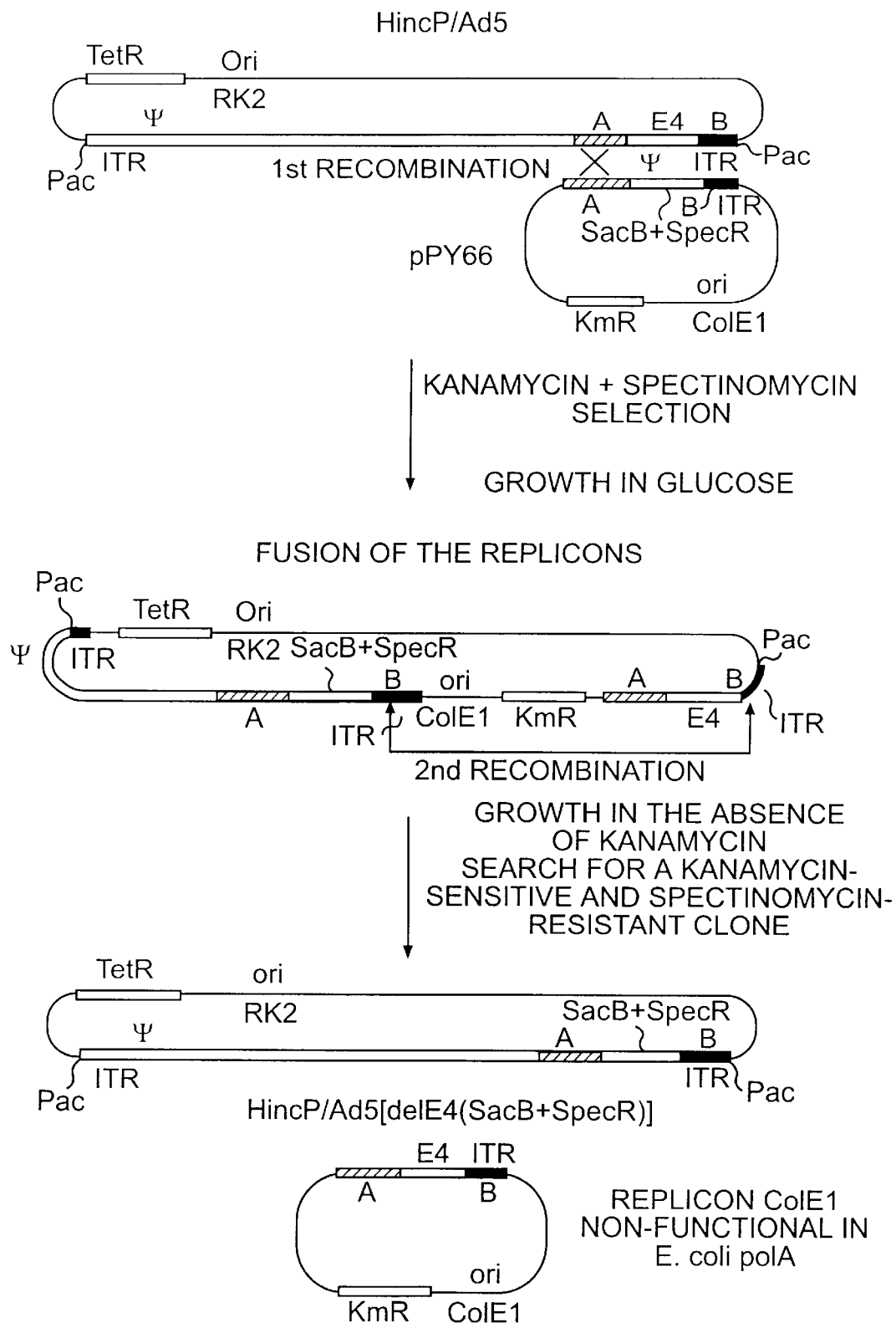

FIG. 16: (A): Diagrammatic representation of a homologous recombination between the replicon HincP/Ad5 and plasmid pPY66.

FIG. 16(B): Protocol for generating the HincP/Ad5 [delE4-(Y+ITR)] viral genome via homologous recombination of the two replicons pPY82 and HincP/Ad5[delE4 (SacB+SpecR)].

Figure 17:
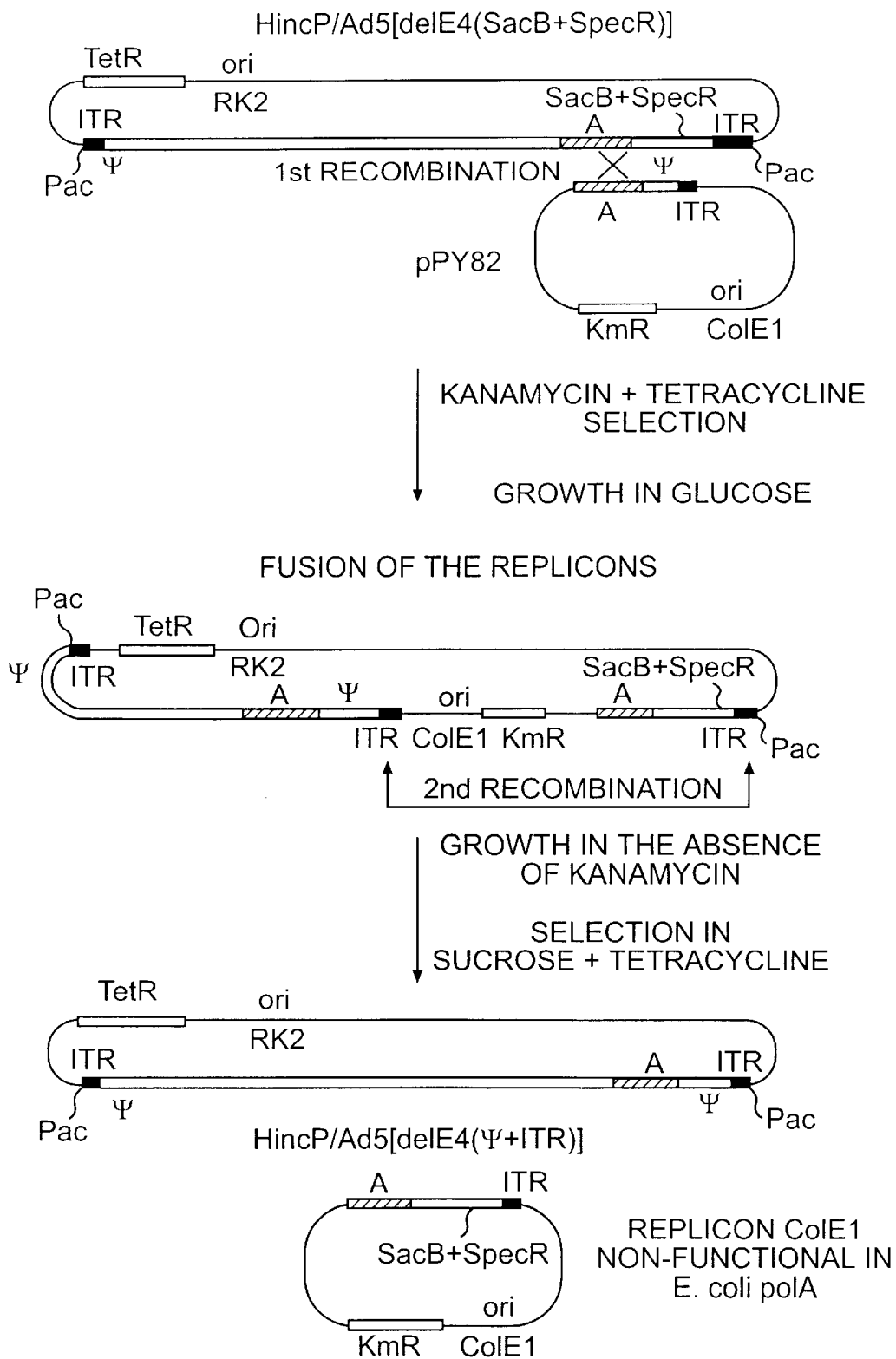

FIG. 17: Diagram of plasmids pPY88, pGY50' and pPY90'.

Figure 18:
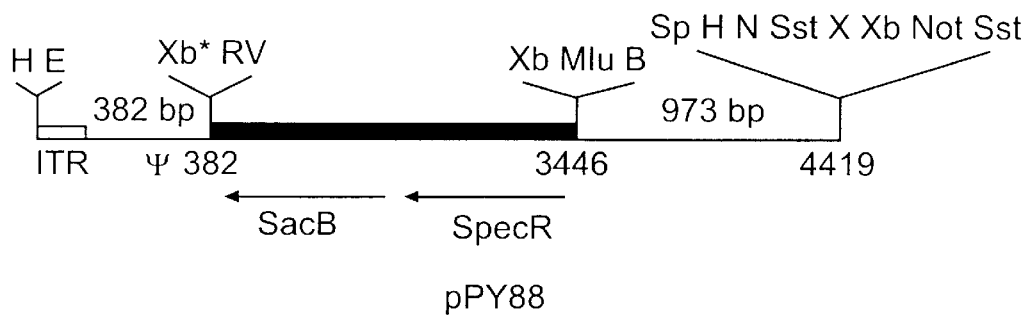
Figure 18:
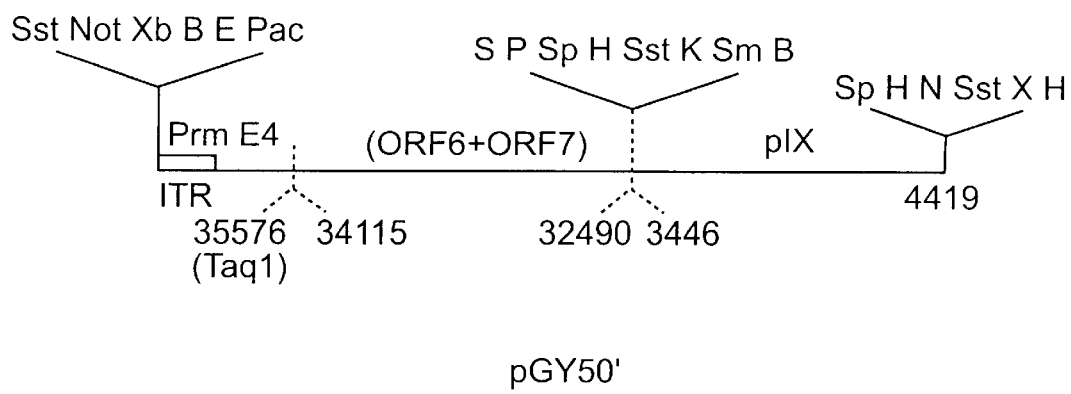
Figure 18:
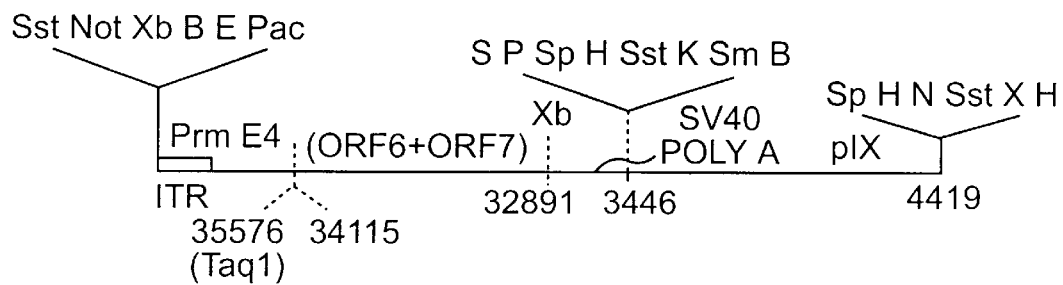

FIG. 18: Restriction maps of the plasmids pPY88, pPY50' and pPY90'.

Figure 19:
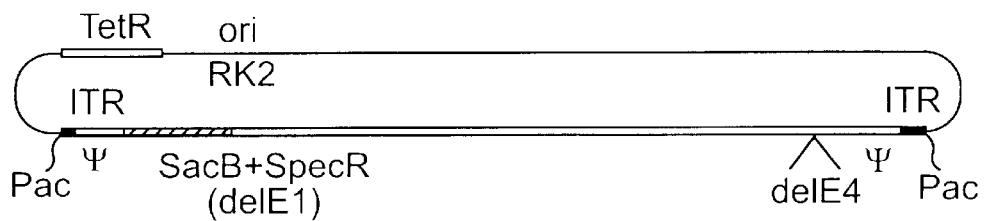
Figure 19:
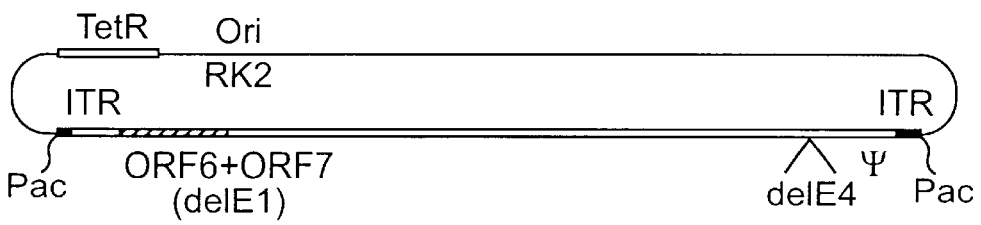

FIG. 19: Diagram of HincP/Ad5(ITRYdelE1(SacB+SpecR)-delE4(Y+ITR)] and HincP/Ads[ITRYdelE1(ORF6+ORF7)delE4-(Y+ITR)].

Figure 20:
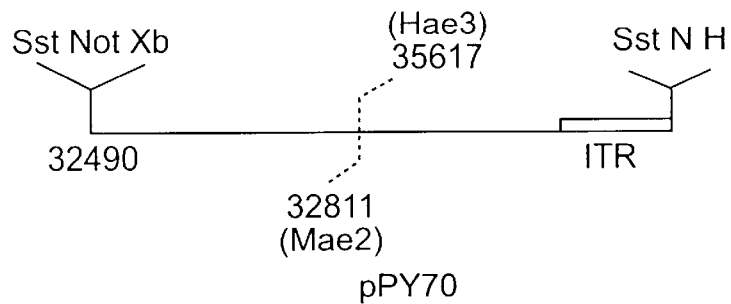
Figure 20:
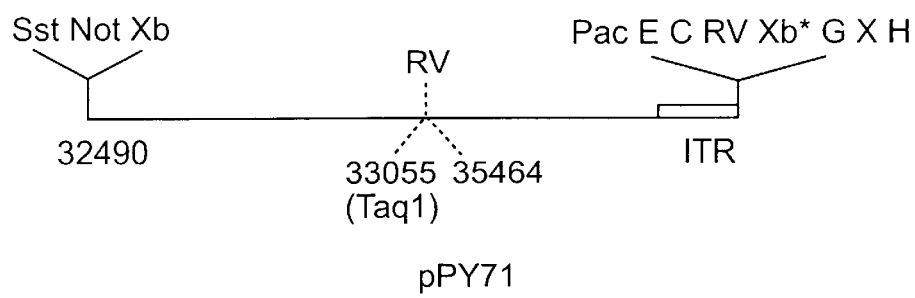
Figure 20:
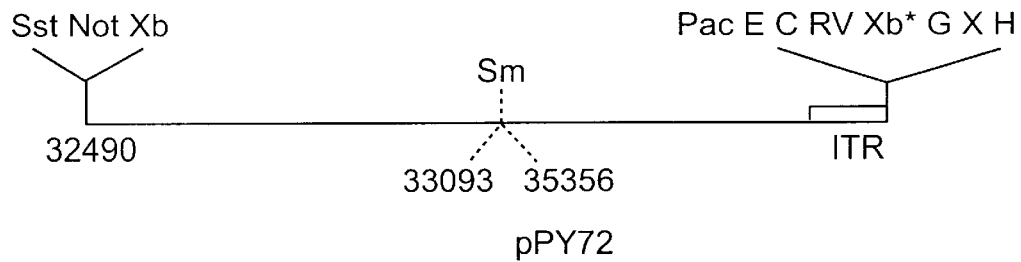

FIG. 20: Restriction maps of the plasmids pPY70, pPY71 and pPY72.

Figure 21:
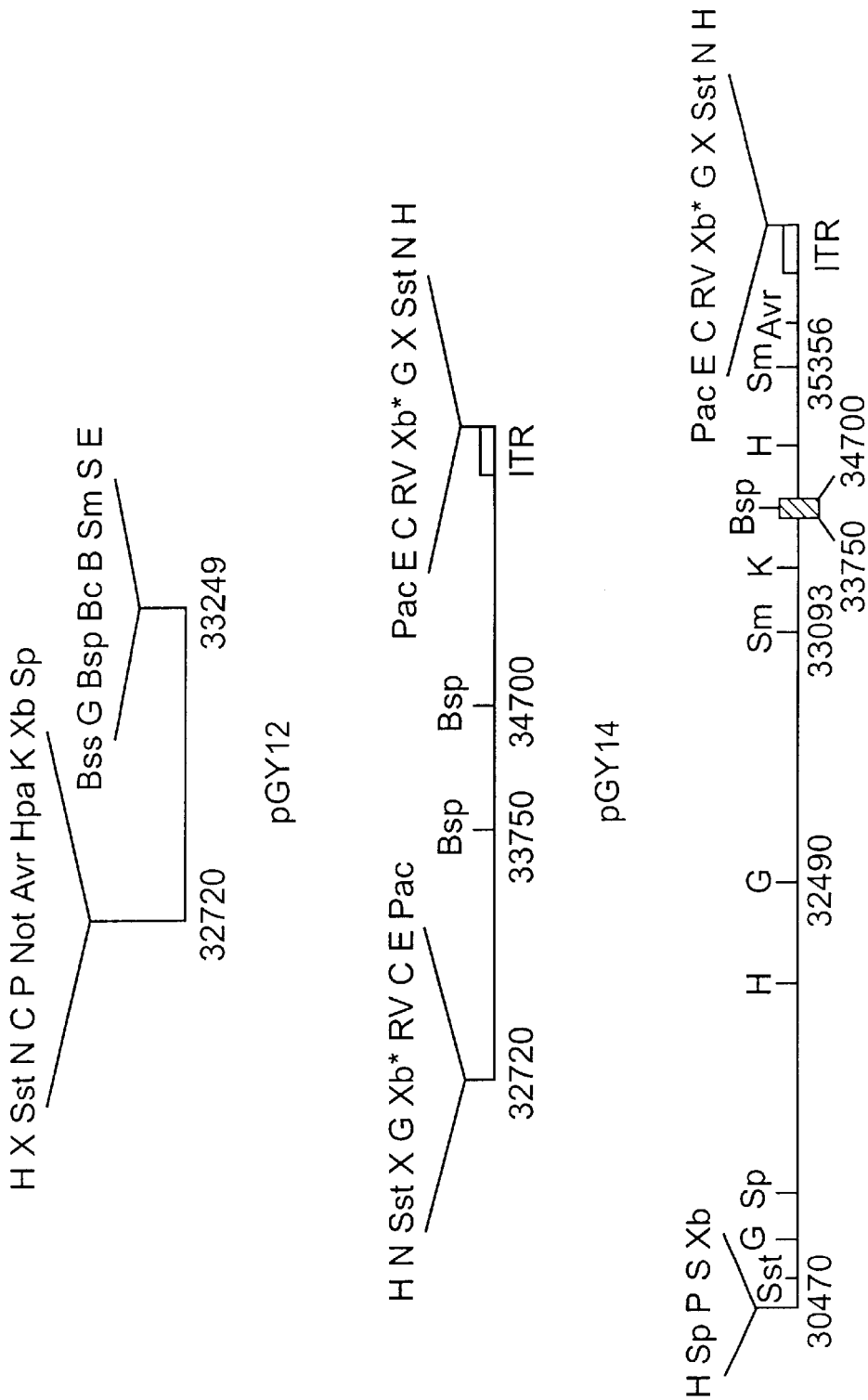

FIG. 21: Restriction maps of the plasmids pGY12, pGY14 and pMC2.

Figure 22:
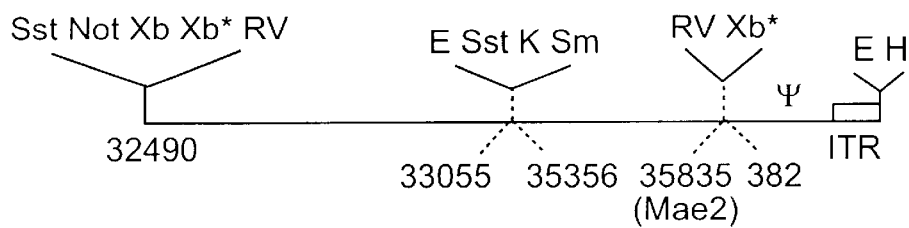
Figure 22:
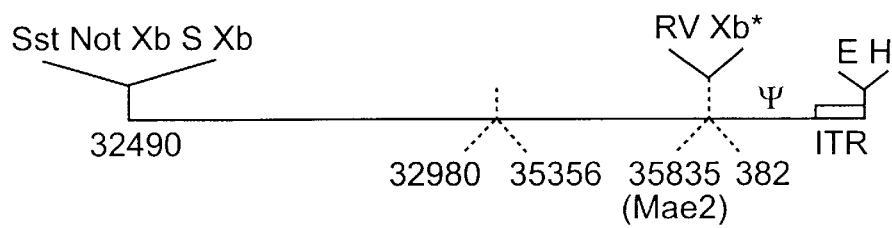
Figure 22:
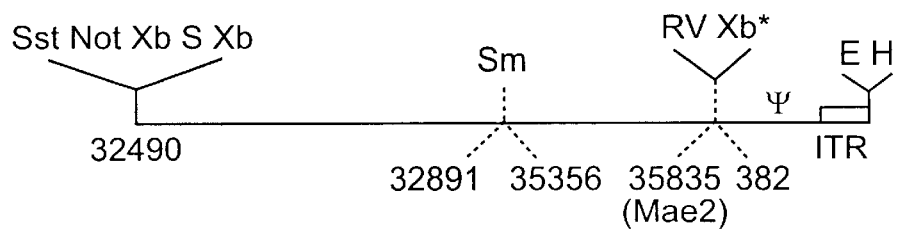

FIG. 22: Restriction maps of the plasmids pPY91, pPY94 and pPY92.

Figure 23:
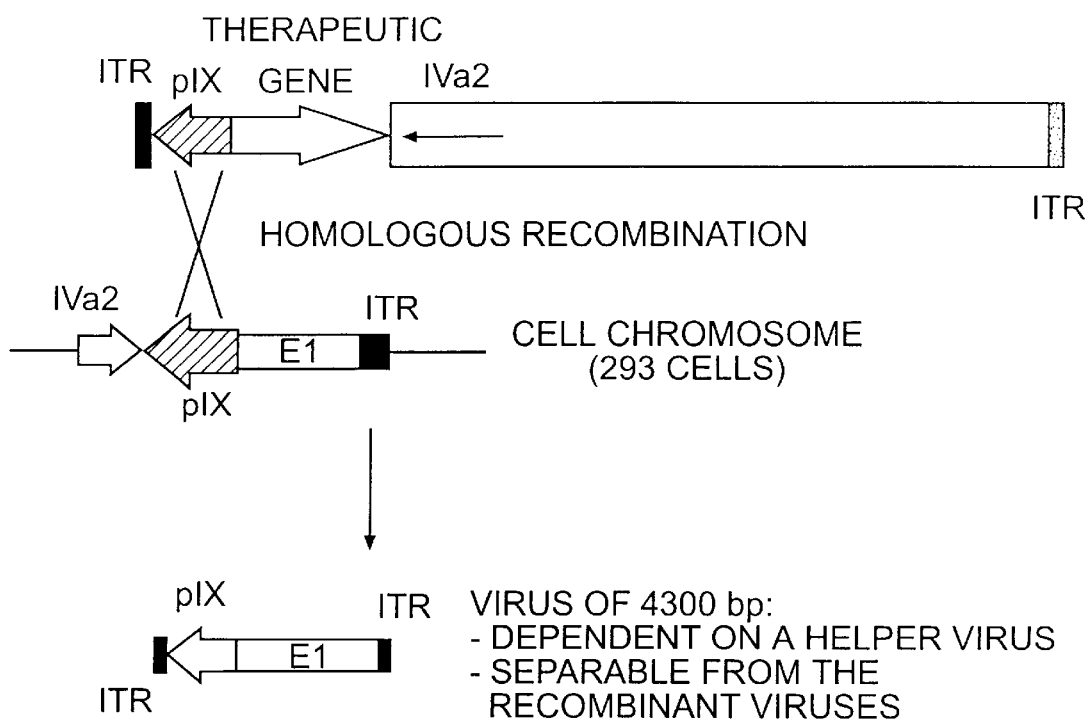

FIG. 23: Protocol for preparation of defective viruses according to the invention.

GENERAL TECHNIQUES OF MOLECULAR BIOLOGY

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol-chloroform extraction of proteins, ethanol or isopropanol precipitation of DNA in a saline medium, transformation in Escherichia coli, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories). To carry out ligation, the DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations. The filling in of 5' protruding ends may be performed with the Klenow fragment of E. coli DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

In vitro site-directed mutagenesis using synthetic oligodeoxynucleotides may be performed according to the method developed by Taylor et al. [Nucleic Acids Res. 13 (1985) 8749–8764] using the kit distributed by Amersham. The enzymatic amplification of DNA fragments by the so-called PCR [polymerase-catalysed chain reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications. Verification of the nucleotide sequences may be performed by the method developed by Sanger et al. [Proc. Natl. Acad. Sci. USA, 74 (1977) 5463–5467] using the kit distributed by Amersham.

EXAMPLE 1
Construction of Plasmid PCO1 (FIG. 7)

A—Construction of the Plasmid pCE

The EcoRI-XbaI fragment corresponding to the left-hand end of the Ad5 adenovirus genome was first cloned between the EcoRI and XbaI sites of the vector pIC19H. This generates the plasmid pCA. Plaumid pCA was then cut with HinfI, its 5' protruding ends were filled in with the Klenow fragment of E. coli DNA polymerase I and it was then cut with EcoRI. The fragment of plasmid pCA thus generated, which contains the left-hand end of the Ad adenovirus genome, was then cloned between the EcoRI and SmaI sites of the vector pIC20H (Marsh et al., Gene 32 (1984) 481). This generates the plasmid pCB. Plasmid pCB was then cut with EcoRI, its 5' protruding ends were filled in with the Klenow fragment of E. coli DNA polymerase I and it was then cut with BamHI. The fragment of plasmid pCB thus generated, which contains the left-hand end of the Ad5 adenovirus genome, was then cloned between the NruI and BglII sites of the vector pIC20H. This generates the plasmid pCE, an advantageous feature of which is that it possesses the first 382 base pairs of the Ad5 adenovirus, followed by a multiple cloning site.

B—Construction of the Plasmid pCD'

The Sau3A (3346)-SstI (3645) fragment and the SstI (3645)-NarI (5519) fragment of the Ad5 adenovirus genome were first ligated and cloned between the ClaI and BamHI sites of the vector pIC20H, thereby generating the plasmid pPY53. The SalI-TaqI fragment of plasmid pPY53 prepared from a dam-context, containing the portion of the Ad5 adenovirus genome lying between the Sau3A (3346) and TaqI (5207) sites, was then cloned between the SalI and ClaI sites of the vector pIC20H, thereby generating the plasmid pCA'. The TaqI (5207)-NarI (5519) fragment of the Ad5 adenovirus genome prepared from a dam-context and the SalI-TaqI fragment of plasmid pCA' were then ligated and cloned between the SalI and NarI sites of the vector pIC20H. This generates the plasmid pCC'. The NarI (5519)-NruI (6316) fragment of the Ad5 adenovirus genome prepared from a dam-context and the SalI-NarI fragment of plasmid pCC' were then ligated and cloned between the SalI and NruI sites of the vector pIC20R. This generates plasmid pCD'.

C—Construction of Plasmid pCO1

A partial digestion with XhoI followed by a complete digestion with SalI of plasmid pCD' generates a restriction fragment which contains the Ads adenovirus sequence from the Sau3A site (3446) to the NruI site (6316). This fragment was cloned into the SalI site of plasmid pCE. This generates plasmid pC01 (FIG. 7), which contains the left-hand portion of the Ad5 adenovirus up to the HinfI site (382), a multiple cloning site and the Sau3A (3446)-NruI (6316) fragment of the Ad5 adenovirus.

EXAMPLE 2
Construction of Plasmids of the pCO1-E4 type (FIG. 7)

This example describes the construction of plasmids of the pCO1-E4 type, that is to say plasmids obtained by incorporation of all or a functional portion of the E4 region of an adenovirus in plasmid pCO1 (Example 1).

2.1. Cloning of the E4 Region in its Entirety 2.1.1. Expressed from the Original Promoter of the E4 Region The plasmid pPY2 corresponds to the cloning of the Avr2-Sal1 fragment (approximately 1.3 kb including the promoter/LTR of the MMTV virus) of plasmid pMSG (Pharmacia) between the Xba1 and Sal1 sites of plasmid pIC20H prepared from an E. coli dam+ context.

The plasmid pPY4 is derived from plasmid pPY2 by deletion of a 35-bp fragment after cleavage with BamH1 and Bgl2 followed by religation.

The plasmid pPY5 corresponds to the cloning of the Taq1-Bgl2 fragment (positions 35576–32490) including the E4 region of Ad5 between the Cla1 and BamH1 sites of plasmid pIC20H. In this plasmid, the whole of the E4 region of Ads is hence now flanked by EcoRV and Sph1 sites originating from the multiple cloning site. Partial digestion of plasmid pPY5 with EcoRV followed by a digestion with Sph1 enables an approximately 3.1-kb EcoRV-Sph1 fragment including the whole of the E4 region of Ad5 to be purified.

Cloning of this EcoRV-Sph1 fragment between the Sma1 and Sph1 sites of plasmid pPY4 generates plasmid pPY6 (FIG. 8).

The plasmid pPY6* is identical to plasmid pPY6, with the exception of the Xba1 site which has been destroyed after cleavage by filling in using the Klenow fragment of *E. coli* DNA polymerase (Biolabs), followed by religation. Plasmid pPY6* hence contains the whole of the E4 region (from the Taq1 site at position 35576 and up to position 32490 localized approximately 300 bp after the polyadenylation site) expressed under the control of the LTR promoter of the RSV virus.

Plasmid pFG144 [F. L. Graham et al., EMBO J. (1989) 8 2077–2085] contains, in particular, a 1162-bp Sau3A fragment including the right-hand end of the Ad5 genome from position 34773. This fragment is then cloned L. into the BamHI site of plasmid pIC20H, thereby generating the plasmid pGY9 in which the Sau3A fragment is now included in a 1184-bp BamHI-EcoRI fragment as a result of the orientation of the fragment relative to the vector. This fragment is then purified by electroelution, cut with AvrII and then subjected to a partial hydrolysis with the enzyme MaeII. One of the restriction products corresponds to the MaeII (35835)-AvrII (35463) fragment which includes the promoter of the E4 region of Ad5 and up to the limit of the right-hand ITR. This 372-bp fragment is then purified by electroelution and ligated in the presence of the AvrII-SalI fragment of plasmid pPY6* between the ClaI and SalI sites of plasmid pCOI, thereby generating the plasmid pGY10 (FIG. 9) which is of the pCOI-E4 type (FIG. 7).

2.1.2. Expressed from a Heterologous Promoter
i) Expression from the LTR of the MMTv Virus Plasmid pPY6 is the source of an approximately 4.5-kb Xho1-Sal1 fragment corresponding to the MM LTR/E4 expression cassette. Cloning of this cassette at the Sal1 site of plasmid pCO1 generates the plasmid pCO1-MMTV/E4 (2 possible orientations of the E4 region with respect to the ITR and to the ψ sequence) which is of the pCO1-E4 type.
ii) Expression from the pGRE5 Promoter Cloning of the Xba1 fragment (approximately 1 kb) of the plasmid pGRE5.1 includes an expression cassette composed of a minimal promoter which is highly inducible with glucocorticoids and a polyadenylation signal [Mader and White Proc. Natl. Acad. Sci. (1993) 90 5603–5607]. Cloning of this fragment between the Xba1 sites of plasmid pIC20H, prepared from a dam– context, generates plasmid pPY21 in which the 5 binding sites for the glucocorticoid receptor are now localized in immediate proximity to the Bgl2 site originating from the multiple cloning site. Plasmid pPY21 is the source of an approximately 0.8-kb Bgl2-EcoR1 fragment corresponding to the minimal promoter which is highly inducible with glucocorticoids. Cloning of this fragment between the Bgl2 and EcoR1 sites of plasmid pIC20H generates the plasmid pPY26.

The plasmid pPY5 is the source of an approximately 0.65-kb EcoRV-Hind3 fragment which includes the Taq1-Hind3 fragment from positions 35576 to 34930 on the Ad5 genome. Cloning of this fragment between the EcoRV and Hind3 sites of plasmid pIC20R generates the plasmid pPY24 in which an EcoR1 site is now localized in proximity to the Taq1 site (position 35576). Cloning of the EcoR1-Hind3 fragments (0.65 kb) of plasmid pPY24 and of the Hind3-Sph1 fragment (approximately 2.4 kb including the Ad5 DNA between positions 34930 and 32490) of plasmid pPY5 between the EcoR1 and Sph1 sites of plasmid pIC20E generates the plasmid pPY37. This plasmid is the source of an approximately 3.1-kb EcoR1-Sph1 fragment which contains the whole of the E4 region of Ad5 from positions 35576 to 32490. Cloning of this fragment between the EcoR1 and Sph1 sites of plasmid pPY26 generates the expression plasmid pPY40 (FIG. 8) in which the E4 region is expressed from the pGRE5 promoter. In this plasmid, the 1st splicing donor site of the E4 region is retained. The pGRE5/E4 expression cassette of plasmid pPY40 is available in the form of an approximately 3.9-kb Bgl2-Sal1 fragment, cloning of which between the BamH1 and Sal1 sites of plasmid pCO1 generates the plasmid pCO1-pGRE5/E4 which is of the pCO1-E4 type (FIG. 7).

2.2. Cloning of a Functional E4 Subregion
2.2.1. Expressed from the Original Promoter of the E4 Region
i) Minimal ORF6+ORF7 Sequence The plasmid pGY47' corresponding to the cloning of the Bgl2-Sal1 fragment (which includes the E4 region of Ad5 from positions 34115 to 32490, equivalent to the whole of the ORF6 and ORF7 reading frames of the E4 region) of plasmid pPY6 between the corresponding sites of plasmid pIC20R. In plasmid pGY47', the ORF6+ORF7 region of the E4 region is now included in an approximately 1.65-kb Cla1-Sal1 fragment.

The Mae2-Avr2 fragment corresponding to the Ad5 sequence from positions 35835 to 35464 is purified by electroelution after partial hydrolysis with Mae2 and total hydrolysis with Avr2. This fragment is then hydrolysed with Taq1, and the Mae2-Taq1 fragment (positions 35835 to 35576) is cloned in the presence of the Cla1-Sal1 fragment (1.65 kb) originating from plasmid pGY47' between the Cla1 and Sal1 sites of plasmid pCO1. One of the products of the reaction corresponds to the plasmid pCO1-(ORF6+ORF7) (FIG. 10) which is of the pCO1-E4 type.

In another especially advantageous exemplification, the sequence located between the stop codon of ORF7 and the Bgl2 site (up to position 32490, thereby including the polyadenylation site of E4)is deleted and replaced by a heterologous polyadenylation site. Thus, the Xba1-Sal1 fragment (approximately 0.25 kb) corresponding to the "late" polyadenylation signal of the SV40 virus is isolated from the plasmid pGL3 and cloned between the corresponding sites of plasmid pIC20H, prepared from a dam+ context, thereby generating the plasmid pPY76. Cloning of the Kpn1-BssH2 fragment (positions 33598 to 33249 on the Ad5 genome) and BssH2-Sau3A fragment (positions 33249 to 32891) between the Kpn1 and BamF1 sites of plasmid pPY76 generates the plasmid pPY77 (FIG. 11). This plamid is the source of a Kpn1-Sal1 fragment (approximately 0.7 kb including the sequences lying between positions 33598 and 32891), cloning of which between the corresponding sites of plasmid pCO1-(ORF6+ORF7) generates the plasmid pPY78 (FIG. 11) which is of the pCO1-E4 type.
ii) ORF6 Sequence Only Cloning of the Kpn1-BssH2 fragment (positions 33598 to 33249 on the Ad5 genome) and BssH2-Pvu2 fragment (positions 33249 to 33126) between the Xpn1 and Sma1 sites of plasmid pPY76 generates the plasmid pPY79. This plasmid is the source of a Kpn1-Sal1 fragment (approximately 0.5 kb including the sequences lying between positions 33598 and 33126), cloning of which between the corresponding sites of plasmid pCO1-(ORF6+ORF7) generates the plasmid pCO1-(ORF6) which is of the pCO1-E4 type.

iii) ORF3 Sequence Only

A plasmid of the pCO1-E4 type in which only the ORF3 reading frame of the E4 region is present may also be constructed in a similar manner. In effect, it is known that the expression of ORF3 alone is sufficient to complement viruses from which the E4 region has been deleted.

2.2.2. Expressed from a Heterologous Promoter i) Expression from the LTR of the MTV Virus The Bgl2-Xba1 fragment (approximately 1.65 kb) of plasmid pPY6 includes the Ad5 sequence between positions 34115 and 32490 (ORF6+ORF7 of the E4 region). Cloning of this fragment between the Bgl2 and Xba1 sites of plasmid pIC20H generates the plasmid pPY13. This plasmid now contains the E4 (ORF6+ORF7) subregion of Ad5 in an approximately 1.65-kb Xho1-Sph1 fragment. Cloning of this fragment between the Sal1 and Sph1 sites of plasmid pPY4 generates the plasmid pPY15 (FIG. 12) which contains an approximately 3.1-kb Xho1-Sal1 fragment corresponding to a cassette for the expression of (ORF6+ORF7) of the E4 region of Ad5 under the control of the LTR promoter of the MMTV virus. Cloning of this fragment at the Sal1 site of plasmid pCO1 generates the plasmid pCO1-MMTV/-(ORF6+ORF7) which is of the pCO1-E4 type.

ii) Expression from the pGRES Promoter

The Bgl2-Sal1 fragment of the plasmid pPY13 (approximately 1.65 kb) includes the E4 (ORF6+ORF7) subregion of Ad5. Cloning of this fragment between the BamH1 and Sal1 sites of plasmid pIC20H generates the plasmid pPY45 in which the (ORF6+ORF7) subregion is now included in an approximately 1.65-kb EcoR1-Sph1 fragment. Cloning of this fragment between the EcoR1 and Sph1 sites of plasmid pPY26 generates the plasmid pJY1 (FIG. 12) which includes a cassette for the expression of the (ORF6+ORF7) subregion expressed from the pGRE5 promoter in the form of an approximately 2.5-kb Bgl2-Sal1 fragment. Cloning of this Bgl2-Sal1 fragment between the BamH1 and Sal1 sites of plasmid pCO1 generates the plasmid pCO1-pGRE5/-(ORF6+ORF7) which is of the pCO1-E4 type (FIG. 7).

EXAMPLE 3
Construction of Recombinant Adenoviruses Derived from Plasmids of the DCO1-E4 Type This example describes the construction of recombinant adenoviruses carrying a deletion in the E1 region extending from nucleotide 382 to nucleotide 3446, an inactivated E4 region, and all or a functional portion of E4 inserted into the E1 deletion.

The techniques for a person skilled in the art enable $E1^-E4^+$ recombinant adenoviruses to be constructed and propagated in line 293. Plasmids of the pCOI-E4 type may, for example, be cotransfected into 293 cells in the presence of a viral genome carrying a modification/deletion in the E4 region such that this region is non-functional (mutation in ORF3 and ORP6 at least). Such viruses are hence non-viable in a line which does not functionally trans-complement the E4 region. In contrast, these viruses can be propagated beforehand in line W162 [Weinberg and Ketner Proc. Natl. Acad. Sci. (1983) 80: 5383–5386] or in one of the 293E4+ lines described in Patent FR 94/04590 (18.04.1994). Such viruses include the viruses Ad2dl808 [Challberg and Ketner Virology (1981) 114: 196–209], Ad5dl1004, Ad5dl1007 or Ad5dl1014 [Bridge and Ketner J. Virol. (1989) 63: 631–638] or alternatively Ad5dl1011 [Bridge et al., Virology (1993) 193: 794–801], and the like. Thus, the cotransfection of plasmids of the pCOI-E4 type linearized with the enzyme XmnI and the viral genomic DNA of viruses carrying a non-functional E4 region and restricted with the enzyme ClaI generates the corresponding viruses after homologous recombination between the two DNAs in line 293. These viruses are hence distinguished by the presence of the left-hand ITR and of a functional encapsidation sequence (sequence ψ, nucleotides 1–382, for example), followed by a functional E4 region (complete or at least ORF3 or ORF6) expressed from a functional promoter, and for example the original promoter of the E4 region [included in the TaqI (35576)-MaeII(35835) fragment], or an inducible promoter, followed by the region located down-stream of the Sau3A site localized at position 3446 of the Ad5 genome, and continuing up to the right-hand ITR and hence including the deletion of the E4 function present in the initial $E4^-$ virus (FIG. 13). For example, $E1^-E4^+$ viruses distinguished by an E4 deletion on the right-hand side of the genome originating from the virus Ad5d1011 may be propagated in line 293 at titres above $10^{11}$ PFU/ml.

EXAMPLE 4
Introduction of the ψ Sequence on the Right-hand Side of the Viral Genome 4.1. Introduction of a (SacB+SpecR) cassette into the E4 region 4.1.1. Construction of the Plasmid PPY66

The Bcl1-Acr2 fragment (approximately 0.5 kb) originating from the plasmid pFG144 corresponds to the right-hand end of the Ad5 genome from the Avr2 site at position 35464. Cloning of this fragment between the Xba1 and BamH1 sites of plasmid pIC19H prepared from an *E. coli* dam– context generates the plasmid pPY23. This plasmid is the source of an approximately 320-bp Sal1-Hae3 fragment including the right-hand end of the Ad5 genome up to the Hae3 site at position 35617. Cloning of this fragment between the Xho1 and EcoRV sites of plasmid pIC2OH generates the plasmid pPY29.

The Bgl2-Sma1 fragment corresponding to the Ad5 genome between positions 32490 and 33093 is then cloned between the BanH1 and Sma1 sites of plasmid pPY29, thereby generating the plasmid pPY64. This plasmid is the source of an Xba1-Hind3 fragment, cloning of which between the corresponding sites of the multiple cloning site of the plasmid pXL2675 (FIG. 14) generates the plasmid pPY65. Plasmid pXL2675 (2513 bp) is a replicon of the ColE1 type (included in the approximately 1.15-kb BsA1-Pvu2 fragment and originating from the commercial plasmid pBKS+), possessing a gene conferring kanamycin resistance (originating from Tn5, Pharmacia plasmid pUCKXXX) in *E. coli* and a synthetic multiple cloning site.

The plasmid pXL2757 (FIG. 14) is the source of an approximately 4-kb Sma1-EcoRV fragment containing the SacB gene of B. subtilis and a gene conferring spectinomycin resistance in *E. coli*. The (SacB+SpecR) cassette of this fragment, cloned into the Sma1 site of plasmid pPY65, generates the plasmid pPY66 (FIG. 15).

4.1.2. Construction of the Viral Genome in *E. coli*

Plasmid pPY66 can be used to introduce the (SacB+SpecR) cassette by homologous recombination with a viral genome derived from Ad5 and included in a replicon which is functional in *E. coli* polA. The technology, described in Patent Application FR 95/016323, is based on the use of certain properties of replication in *E. coli*. In effect, replicons of the incompatibility class HincP (and for example RK2) replicate in the absence of the enzyme encoded by the polA gene. Conversely, replicons of the ColE1 type (plasmids of the pUC, pIC, pBR, and the like, type) require this enzyme in order to replicate. On the basis of this observation, the Ad5 genome derived from plasmid pFG144 was first cloned into the plasmid RK2 (of the HincP class) and then introduced by electroporation into an *E. coli* strain mutated in the polA gene. The Xba1 fragment which contains the replicon ColE1 (pBR), included in place of the E3 region in plasmid pFG144, was then deleted from the genome (Patent Application FR 95/016323). This generates the E. coli strain referred to as *E. coli* polA/Ad5. An important point is that the adenoviral genome present in this strain is flanked by Pac1 sites on each side of the ITRs, and that such genomes are infectious after transfection into 293 cells.

The introduction of the (SacB+SpecR) cassette by homologous recombination in *E. coli* polA/Ad5 is performed in the following manner:

a) Plasmid pPY66 is first introduced by electroporation into the *E. coli* polA/Ad5. A selection in the presence of spectinomycin and kanamycin is performed. Resistant clones then correspond to the formation of a cointegrate between the replicon HincP/Ad5 and plasmid pPY66. In virtually all cases, there has been insertion of plasmid pPY66 by a homologous recombination event between the two types of replicon. A clone corresponding to the outcome of a recombination in the E4 region between positions 32490 and 33093 (603 bp) is then isolated (FIG. 16A).

b) This bacterial clone possesses a "direct repeat" of the sequences (A and B) on each side of the (SacB+SpecR) cassette: 603 bp on the one hand and 320 bp (right-hand end of the genome) on the other hand. The presence of such sequences is a source of instability and gives rise to rare homologous recombination events on each side of the (SacB+SpecR) cassette. These homologous recombination events result in the ejection of the colE1 replicon and hence in the loss of the kanamycin-resistance marker. The most numerous recombination event take place in the 603-bp sequence, and are of no value since they regenerate the starting situation, i.e. an adenoviral genome having an unmodified E4 region, and such recombinants have lost their spectinomycin-resistance character since they no longer possess the (SacB+SpecR) cassette. They are hence sensitive to this antibiotic and are, furthermore, capable of growing in the presence of sucrose as carbon source. In contrast, a homologous recombination event in the 320 bp at the right-hand end of the genome (sequence B) leads to the loss of the E4 region initially present, and to its replacement by the (SacB+SpecR) cassette (FIG. 16A). This generates *E. coli* clones referred to as *E. coli* polA/Ad5[delE4(SacB+SpecR)]. Such clones are spectinomycin-resistant and are incapable of growing in the presence of sucrose as unique carbon source. An *E. coli* clone possessing such a genome modified at the right-hand end is isolated as a result of its "kanamycin-sensitive", spectinomycin-resistant phenotype and sensitivity to sucrose.

4.2. Introduction of the 0 Sequence on the Right-hand Side of the Viral Genome 4.2.1. Construction of the Plasmid pPY82

The Sal1-Sma1 fragment originating from plasmid pPY6* and corresponding to the Ad5 genome from positions 32490 to 33093 is first cloned between the corresponding sites of the plasmid pCO7, thereby generating the plasmid pPY81. Plasmid pCO7, obtained after total restriction of plasmid pCO1 with Pst1 and religation, hence contains the left-hand end of Ad5 up to position 382 and the multiple cloning site of plasmid pCO1, followed by the Ad5 sequence from position 3446 up to the Pst1 site localized at positions 3788. Plasmid pPY81 is the source of an approximately 1.4-kb H3-Xba1 fragment, cloning of which between the corresponding sites of plasmid pXL2675 generates the plasmid pPY82, a restriction map of which is given in FIG. 15.

4.2.2. Construction of the Viral Genome in *E. coli*

Introduction of the ψ sequence in immediate proximity to the right-hand ITR is also accomplished by homologous recombination after introduction of plasmid pPY82 by electroporation into *E. coli* generates the viral genome HincP/Ad5[delE4(ψ+ITR)]. The replicon fusion event is first selected in the presence of kanamycin. A clone corresponding to a homologous recombination event between the sequences 32490 and 33093 common to both replicons is then isolated (FIG. 16B). The ejection event of the replicon ColE1 (originating from plasmid pXL2675) is then amplified by lifting the kanamycin selection for a sufficient number of generations. Glucose as carbon source is then replaced by sucrose, and the bacterial clones for which the replicon ColE1 ejection event has taken place by homologous recombination in the ITR is thus isolated, thereby generating the viral genome HincP/Ad5[delE4(ψ+ITR)] (FIG. 16B). A clone corresponding to this event is then isolated: *E. coli* polA/Ad5-[delE4(ψ+ITR)].

EXAMPLE 5

Development for Construction which is Useful for Obtaining a Virus Whose Genome Possesses a Deletion of the ψ Sequence on the Left-hand Side 5.1. Introduction of a (SacB+SpecR) Cassette on the Left-hand Side of the Viral Genome The Hind3-EcoRV fragment (approximately 0.4 kb) of plasmid pCO1 includes the left-hand end of the viral genome up to position 382. Cloning of this fragment between the corresponding sites of plasmid pXL2675 generates the plasmid pPY83. The plasmid pCO1DSal is obtained after digestion of plasmid pCO1 (prepared in a dam+ context) with the enzyme Xba1, treatment with the Klenow fragment of E. coli DNA polymerase I and then religation. This plasmid is the source of an approximately 1-kb BamR1-Nsi1 fragment which includes the Ad5 sequences from positions 3446 to 4419 (NsiI site). Cloning of this fragment between the BamH1 and Pst1 sites of plasmid pIC2OR generates the plasmid pPY86, in which the sequences lying between positions 3446 and 4419 are now included in a BamH1-Bgl2 fragment. Cloning of this fragment at the BanH1 site of plasmid pPY83 generates the plasmid pPY87. The Sma1-EcoRV fragment corresponding to the (SacB+SpecR) cassette of plasmid pXL2757 is then cloned into the EcoRV site of plasmid pPY87, thereby generating the plasmid pPY88 (FIG. 17). This plasmid is used to replace, according to a procedure similar to the procedure described in FIG. 16A, the left-hand portion of the HincP/Ad5[delE4(ψ+ITR)] genome by the corresponding portion originating from plasmid pPY88, thereby generating the viral genome designated HincP/Ad5 [ITRψdelE1(SacB+SpecR)delE4(ψITR)], the structure of which is given in FIG. 18.

5.2. Deletion of the ψ Sequence and Introduction of a Functional E4 Region 5.2.1. Construction of the Plasmid pGY50'

The right-hand end of the adenovirus genome was amplified by PCR with the oligonucleotides 5'-CGGCGG GAATTCTTAATTAACATCATCAATAATATACCTTATTTTGG-3' (SEQ ID No. 2) (the EcoR1 and Pac1 sites are underlined) and 5'-CACCAC CTGCAGGGCAGCCATAACAGTCAGCCTTACC-3' (SEQ ID No. 3) (the Pst1 site is underlined) using the plasmid pY23 as substrate (this plasmid contains the right-hand end of the adenoviral genome up to the Avr2 site localized at position 35464). PCR amplification hence generates a 418-bp fragment corresponding to the right-hand end of Ad5, and into which a Pac1 site and then an EcoR1 site have been introduced immediately upstream of the ITR, while a Pst1 site is localized in immediate proximity to position 35517. Cloning of this fragment between the EcoR1 and Pst1 sites of plasmid pUC19 generates the plasmid pXL2624 (see Patent Application FR 95/016323).

The EcoR1-Taq1 fragment of plasmid pXL2624, corresponding to the right-hand end of the viral genome from the Taq1 site at position 35576, is cloned between the EcoR1 and Cla1 sites of plasmid pGY47', thereby generating the plasmid pPY89. This plasmid is the source of an approximately 2-kb EcoR1-Sal1 fragment including the right-hand end of the viral genome up to position 35576, and then the E4 (ORF6+ORF7) subregion from positions 34115 to 32490. Cloning of the EcoR1-Sal1 fragment of plasmid pPY89 and Sal1-Nsi1 fragment (including the Ad5 genome from position 3446 to 4419) of plasmid pCO1 between the EcoR1 and Pst1 sites of plasmid pXL2675 generates the plasmid pGY50' (FIG. 17).

5.2.2. Construction of the Plasmid DPY90'

The Kpn1-Sst1 fragment (approximately 0.95 kb) of the plasmid pPY78 corresponds to the C-terminal portion of the E4 region lying between positions 32891 and 33598, immediately followed by the "late" polyadenylation signal of the SV40 virus. Cloning of this fragment between the corresponding sites of plasmid pPY89 generates the plasmid pPY90. This plasmid is the source of an approximately 2-kb EcoR1-Sal1 fragment including the right-hand end of the viral genome up to position 35576, and then the E4 (ORF6+ORF7) subregion from positions 34115 to 32891. Cloning of the EcoR1-Sal1 fragment of plasmid pPY90 and Sal1-Nsi1 fragment (including the Ad5 genome from positions 3446 to 4419) of plasmid pCO1 between the EcoR1 and Pst1 sites of plasmid pXL2675 generates the plasmid pPY90' (FIG. 17).

5.2.3. Introduction of a Functional E4 Region at the Left-hand End

Plasmid pGY50' or pPY90' is used to replace, according to a procedure similar to the procedure described in FIG. 16B, the left-hand portion of the HincP/Ad5[ITRψdelE1-(SacB+SpecR) [delE4(ψ+ITR)] genome by the corresponding portion originating from said plasmids. For example, the use of plasmid pPY90' generates the viral genome designated HincP/Ad5[ITRDψdelE1(ORF6+ORF7)[delE4(ψ+ITR)], the structure of which is given in FIG. 18.

EXAMPLE 6

Development of a Construction Which is Useful for Obtaining a Virus Whose Genome Possesses New E4 Deletions on the Right-hand Side 6.1. In the Absence of the ψ Sequence 6.1.1. Mae2-Hae3 Deletion (32811–35617)

The plasmid pPY32 is described in Patent Application FR 94/04590 (18.04.94). This plasmid is the source of an approximately 0.65-kb Bgl2-Hind3 fragment corresponding to the right-hand end of the Ad5 genome from the Bgl2 site (position 32490) and carrying a deletion between the Mae2 site (position 32811) up to the Hae3 site (position 35617). Cloning of this fragment between the BamH1 and Hind3 sites of plasmid pXL2675 generates the plasmid pPY70, a restriction map of which is given in FIG. 19. This plasmid can be used to introduce the corresponding E4 deletion by homologous recombination, for example in E. coli polA/ Ad5[delE4(SacB+SpecR)].

6.1.2. Taal-Avr2 Deletion (33055–35464)

The plasmid pGY12 corresponds to the cloning of the BssH2-Msc1 fragment (positions 33249–32720) between the BssH2 and EcoRV sites of the commercial plasmid pSL1180 (FIG. 20). Cloning of the EcoR1-Taq1 fragment of plasmid pXL2624 (this fragment corresponds to the right-hand end of the Ad5 genome up to the Taq1 site at position 35576) and Taq1-BssH2 fragment (positions 35576 to 33249) between the EcoR1 and BssH2 sites of plasmid pGY12 generates the plasmid pGY13. This plasmid is hence the source of an EcoR1-Hpa1 fragment (approximately 3.25 kb) including the right-hand end of the Ad5 genome up to position 32720. Cloning of this fragment between the EcoR1 and Sma1 sites of plasmid pIC20H generates the plasmid pGY14 (FIG. 20). This plasmid is the source of an EcoR1-BspH1 fragment corresponding to the right-hand end of the Ad5 genome up to position 34700. Cloning of this fragment with the BspH1-Xba1 fragment of the Ad5 genome (positions 33750 to 30470) between the Xba1 and EcoR1 sites of plasmid pIC20H prepared from a dam+ context generates the plasmid pMC2 (FIG. 20).

The Sph1-Taq1 fragment localized between positions 31224 and 33055 on the Ad5 genome is purified from plasmid pMC2 and then cloned between the Sph1 and Cla1 sites of plasmid pIC20H, thereby generating the plasmid pYJ5. After transfer to an E. coli dam– context, this plasmid is the source of a BglII-XbaI fragment which includes the sequence of the viral genome located between positions 32490 and 33055. This Bgl2-Xba1 fragment is then cloned with the Avr2-Xho1 fragment originating from plasmid pMC2, and including the right-hand end of the viral genome from the Avr2 site localized at position 35464, between the Banw1 and Xho1 sites of plasmid pXL2675, thereby generating the plasmid pPY71 (FIG. 19). This plasmid can be used to introduce the corresponding E4 deletion by homologous recombination, for example in E. coli polA/Ad5[delE4 (SacB+SpecR)].

6.1.3. Sma1-Sma1 deletion (33093–35356)

The plasmid pMC2DSma1 is obtained after total digestion of plasmid pMC2 with Sma1 followed by religation. This plasmid is the source of an approximately 1.2-kb Bgl2-Hind3 fragment including the whole of the right-hand end of the Ad5 genome from position 32490 and carrying a deletion in the E4 region between positions 33093 and 35356. Cloning of this fragment between the BamH1 and Hind3 sites of plasmid pXL2675 generates the plasmid pPY72, a restriction map of which is given in FIG. 19. This plasmid can be used to introduce the corresponding E4 deletion by homologous recombination, for example in E. coli polA/Ad5[delE4(SacB+SpecR)].

6.2. In the Presence of the ψ Sequence 6.2.1. Sma1-Sma1 Deletion (33093–35356)

The BamH1-EcoR1 fragment of the plasmid pGY9 (approximately 1.2 kb) includes the right-hand end of the Ad5 genome from the Sau3A site at position 34773. This restriction fragment is purified by electroelution, cut with Sma1 and then subjected to a partial hydrolysis with the enzyme Mae2. One of the restriction products corresponds to the MaeII (35835)-SmaI (35356) fragment. Cloning of this fragment between the Sma1 and Cla1 sites of plasmid pPY82 generates the plasmid pPY75 (FIG. 15). This plasmid can be used to introduce the corresponding E4 deletion by homologous recombination, for example in E. coli polA/ Ad5[delE4(SacB+SpecR)(ψ+ITR)].

6.2.2. Taq1-Sma1 Deletion(33055–35356)

The Taq1 fragment of plasmid pPY82, which includes positions 32490 (Sal1 site of the multiple cloning site) to 33055, is cloned into the Cla1 site of plasmid pIC20H, thereby generating the plasmid pICTaq in which the Xho1 site of the multiple cloning site is positioned in immediate proximity to position 32490. Plasmid pICTaq is the source of an Xho1-Sma1 fragment including positions 32490 to 33055, cloning of which between the Sal1 and Sma1 sites of plasmid pPY75 generates the plasmid pPY91 (FIG. 21).

6.2.3. Hpa2-Sma1 Deletion (32980–35356)

The Sal1-Hpa2 fragment of plasmid pPY82, which includes positions 32490 to 32980, is cloned between the Sal1 and Cla1 sites of plasmid pIC20H, thereby generating plasmid pPY93. This plasmid is the source of a Sal1-EcoRV fragment including positions 32490 to 32980, cloning of which between the Sal1 and Sma1 sites of plasmid pPY75 generates the plasmid pPY94 (FIG. 21).

6.2.1. Sau3A-Sma1 Deletion (32891–35356)

The Sau3A fragment of plasmid pPY82, which includes positions 32490 to 32891, is cloned into the BamH1 site of plasmid pIC2OH, thereby generating the plasmid pICSau in which the Sal1 site of the multiple cloning site is positioned in immediate proximity to position 32490. Plasmid pICSau is the source of a Sal1-Sma1 fragment including positions 32490 to 32891, cloning of which between the corresponding sites of plasmid pPY75 generates the plasmid pPY92 (FIG. 21).

EXAMPLE 7
Protocol for Transfection of 293 Cells with the Recombinant Genomes Constructed in *E. coli* According to Examples 4 and 5

The construction of the plasmids described according to Examples 4 and 5, or of analogous plasmids which, for example, are distinguished by different E4 deletions or by modified functional E4 regions, or, for example, corresponding to the introduction of a cassette for the expression of a given therapeutic gene, and the like, is used to generate recombinant viral genomes by homologous combination in *E. coli* polA. After verification by restriction, a bacterial clone is then isolated and its plasmid content is extracted and purified. The DNA is then subjected to a total digestion with the enzyme Pac1 and transfected into 293 cells. This DNA is infectious (E1-E4+ virus), and a cytopathic effect (CPE) is apparent after approximately 2 weeks. The CPE is then progressively amplified in 293 cells and a viral stock is prepared (see Patent Application FR 016323).

EXAMPLE 8
Construction for Preparing a Virus in the Genome of Which the pIX Region Has Been Moved 8.1. Construction of the plasmid pCO1-pIX It is useful to modify the orientation of the sequences coding for the viral pIX within the genome, in such a way that a recombination between the cell genome and the viral DNAs do not generate a replicative particle, but a virus containing only its ITRs, the E1A and E1B regions and the sequence coding for pIX. Such a virus is defective and much smaller than the recombinant adenovirus, which enables it to be separated easily by centrifugation on caesium chloride during the preparation of viral stocks (FIG. 22).

The plasmid pCR2-pIX was constructed by cloning the PCR amplification product of plasmid pCO1 with the oligonucleotides 5'-GATATCTGAAGATACAGATTGAG-3' (SEQ ID No. 4) and 5'-CGGCCGTTAAACCGCATTGGGAG-3' (SEQ ID No. 5) into the plasmid pCR2 (Invitrogen).

The plasmid pIC-pIX-pA was constructed by cloning the EcoRV-Eag1 fragment of pCR2-pIX and the Eag1-BanH1 fragment of the plasmid pCI (Promega) containing the polyA of SV40 into plasmid pIC20R digested with EcoRV and BamH1.

The plasmid pCR2-IVa2 was constructed by cloning the PCR amplification product of plasmid pCO1 with the oligonucleotides 5'-AAGCTTATTGCCATCATTATGGAC-3' (SEQ ID No. 6) and 5'-ACTAGTTATTTAGGGTTTTGCGC-3' (SEQ ID No. 7) into plasmid pCR2 (Invitrogen).

The plasmid pIC-IVa2-pA was constructed by cloning the Hind3-Spe1 fragment of pCR2-IVa2 and the Xba1-Sph1 fragment of the plasmid pCDNA3 (Invitrogen), containing the polyadenylation signal of the bovine growth hormone gene, into plasmid pIC20R digested with Hind3 and Sph1. The BstX1-Sal1 fragment of plasmid pIC-IVa2-pA was then cloned between the BstX1-Sal1 sites of plasmid pCO1, thereby creating the plasmid pCO1-_pIX. Plasmid pCO1-pIX was constructed by introducing the Cla1 cassette of pIC-pIX-pA into the Cla1 site of pCO1-_pIX, in such a way that the gene coding for pIX is oriented in the same direction as that coding for IVa2, contrary to its orientation in the adenoviral genome.

Plasmid pCO1-pIX hence contains the ITR-ψ sequences of Ad5, and a cassette for the expression of the pIX of the virus (promoter and gene for pIX followed by the polyA of SV40) oriented in the reverse direction of its natural orientation within Ad5, followed by the IVa2 sequences in which the polyA has been replaced by that of bovine growth hormone. 8.2. Construction of the Virus The recombinant virus was constructed "in the traditional manner" by cotransfection into 293 cells of plasmid pCO1-pIX linearized with Xho1, and with the viral DNA of the virus AdRSVβGal digested with Cla1.

---

What is claimed is:

1. A replication defective recombinant adenovirus having an adenoviral genome, the genome comprising:
 a heterologous nucleic acid sequence which is operatively linked to a transcription promoter region that is functional in an infected cell,
 a first inactivated E1 region, wherein inactivation comprises a deletion or disruption in the E1 region,
 a second inactivated region, wherein inactivation is by deletion in a second essential region selected from the group consisting of a pIX-IVa2 region, an E4 region and an L5 region at its original location in the genome, and
 an insertion of a functional region at a position other than its original position, which complements the second inactivated region and which does not inactivate an additional essential region, wherein the functional region is all or part of an E4 region, a pIX-IVa2 region, or an L5 region,
wherein the deletion in the second essential region does not inactivate an additional essential region which is not complemented by said insertion.

2. The recombinant adenovirus according to claim 1, wherein the functional E4 region is inserted at or within 50 nucleotides of the deletion or disruption in the E1 region.

3. The recombinant adenovirus according to claim 2, further comprising an inactivated E4 ORF3 gene and an inactivated E4 ORF6 gene, and wherein the functional E4 region comprises at least a functional ORF3 gene of E4.

4. The recombinant adenovirus according to claim 1, further comprising an inactivated E4 ORF3 gene and an inactivated E4 ORF6 gene, and wherein the functional E4 region comprises at least a functional ORF6 gene of E4.

5. The recombinant adenovirus according to claim 1, wherein the pIX-IVa2 region is positioned in an E3 region.

6. The recombinant adenovirus according to claim 1, further comprising inactivated E1 and E4 regions at their original positions and all or E1 functional portion of an E4 region present within 50 nucleotides of the inactivated E1 region.

7. The recombinant adenovirus according to claim 1, wherein a region coding for a pIX protein and all or a functional portion of an E4 region are moved from their original positions.

8. The recombinant adenovirus according to claim 7, wherein said regions coding for the pIX protein and all or a functional portion of the E4 region are moved to the E1 region as a replacement for deleted E1 sequences.

9. The recombinant adenovirus according to claim 8, wherein the reading frame of the pIX protein or of the E4 region is placed in the E1 region whereby the orientation of the pIX or E4 region reading frame is preserved.

10. The recombinant adenovirus according to claim 7, wherein the left-hand end of the adenovirus genome, containing an ITR and the encapsidation region, and the right-hand end of said genome, containing an ITR, are interchanged.

11. The recombinant adenovirus according to claim 1, wherein the left-hand end of the adenovirus genome, containing an ITR and the encapsidation region, and the right-hand end of said genome, containing an ITR and all or a functional portion of the E4 region, are interchanged.

12. The recombinant adenovirus according to claim 1, further comprising inactivated E1 and L5 regions at their original positions, wherein a functional L5 region is present within 50 nucleotides of the inactivated E1 region.

13. The recombinant adenovirus according to claim 1, wherein the heterologous nucleic acid sequence comprises one or more therapeutic genes.

14. The recombinant adenovirus according to claim 1, wherein the heterologous nucleic acid sequence is present either at the position of the disrupted E1 or E4 region or as a replacement for the deleted E1 or E4 region.

15. The recombinant adenovirus according to claim 1, wherein the transcription promoter region is a eukaryotic or viral promoter.

16. The recombinant adenovirus according to claim 15, wherein the viral promoter is selected from the group consisting of an E1A, an MLP, a CMV, and an RSV promoter.

17. The recombinant adenovirus according to claim 13, wherein the heterologous nucleic acid sequence further comprises a signal sequence.

18. A replication defective recombinant human adenovirus having an adrenoviral genome, the genome comprising:
 a heterologous nucleic acid sequence which is operatively linked to a transcription promoter region that is functional in an infected cell,
 a first inactivated E1 region, wherein inactivation is by deletion or disruption in the E1 region,
 a second inactivated region selected from the group consisting of a pIX-IVa2 region, an L5 region, and an E4 region, which comprises at least the inactivation of E4 ORF 3 and E4 ORF6 genes, wherein inactivation of the second inactivated region is by deletion of the region at its origin allocation in the genome, and an insertion of a functional region selected from the group consisting of pIX-IVa2, L5 and E4, at a position other than its original position and which does not inactivate an additional essential region, wherein the second inactivated region does not inactivate an additional essential region which is not complemented by the inserted functional region.

19. A defective recombinant adenovirus according to claim 18, wherein the inserted functional region is an E4 ORF3 gene, an E4 ORF6 gene, or both.

20. The recombinant adenovirus according to claim 18, wherein the adenovirus is classified in group C.

21. The recombinant adenovirus according to claim 18, wherein the adenovirus is type 2 (Ad2) or 5 (Ad5).

22. A replication defective recombinant adenovirus having an adenoviral genome, the genome comprising:

a heterologous nucleic acid sequence which is operatively linked to a transcription promoter region that is functional in an infected cell, a first inactivated E1 region, wherein inactivation comprises a deletion or disruption in the E1 region, a second inactivated E3 region, wherein inactivation comprises a deletion or disruption in the E3 region, a third inactivated region, wherein inactivation is by deletion in a third essential region selected from the group consisting of a pIX-IVa2 region, an E4 region and an L5 region at its original location in the genome, and an insertion of a functional region at a position other than its original position, which complements the third inactivated region and which does not inactivate an additional essential region, wherein the functional region is all or part of an E4 region, a pIX-IVa2 region, or an L5 region, wherein the deletion in the third essential region does not inactivate an additional essential region which is not complemented by said insertion.

23. The recombinant adenovirus according to claim 22, wherein the heterologous nucleic acid sequence is present either at the position of the disrupted E1, E3, or E4 region or as a replacement for the deleted E1, E3, or E4 region.

* * * * *